United States Patent [19]

Durant et al.

[11] 4,018,931
[45] Apr. 19, 1977

[54] PHARMACOLOGICALLY ACTIVE THIOUREA AND UREA COMPOUNDS

[75] Inventors: Graham John Durant, Welwyn Garden City; John Colin Emmett, Codicote; Charon Robin Ganellin, Welwyn Garden City, all of England

[73] Assignee: Smith Kline & French Laboratories Limited, Welwyn Garden City, England

[22] Filed: Dec. 4, 1975

[21] Appl. No.: 637,494

Related U.S. Application Data

[60] Division of Ser. No. 451,333, March 14, 1974, Pat. No. 3,950,353, which is a continuation-in-part of Ser. No. 290,584, Sept. 20, 1972, abandoned, which is a continuation-in-part of Ser. No. 230,451, Feb. 29, 1972, abandoned.

[52] U.S. Cl. .............................. 424/269; 424/250; 424/263; 424/270; 424/272; 424/273

[51] Int. Cl.$^2$ ................ A61K 31/41; A61K 31/415
[58] Field of Search .......................... 424/269, 273

[56] References Cited

UNITED STATES PATENTS

| | | | |
|---|---|---|---|
| 3,736,331 | 5/1973 | Black et al. | 260/309 |
| 3,808,336 | 4/1974 | Durant et al. | 424/273 |
| 3,908,014 | 9/1975 | Durant et al. | 424/263 |

Primary Examiner—Norman A. Drezin
Attorney, Agent, or Firm—Joan S. Keps; Richard D. Foggio; William H. Edgerton

[57] ABSTRACT

The compounds are substituted thioalkyl-, aminoalkyl- and oxyalkyl-thioureas and ureas which are inhibitors of histamine activity.

10 Claims, No Drawings

PHARMACOLOGICALLY ACTIVE THIOUREA AND UREA COMPOUNDS

This is a division of application Ser. No. 451,333 filed Mar. 14, 1974, now U.S. Pat. No. 3,950,353, which is a continuation-in-part of Ser. No. 290,584 filed Sept. 20, 1972, now abandoned, which is a continuation-in-part of Ser. No. 230,451, filed Feb. 29, 1972, now abandoned.

This invention relates to pharmacologically active compounds, to pharmaceutical compositions these compounds and to processes for their preparation. The compounds of the invention can exist as the addition salts but, for convenience, reference will be made throughout this specification to the parent compounds.

It has for long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash and Schild (Brit. J. Pharmac. 1966, 27, 427) as H-1. The substances of the present invention are distinguished by the fact that they act at histamine H-2 receptors which, as described by Black et al. (Nature, 1972, 236, 385), are histamine receptors other than the H-1 receptor. Thus they are of utility in inhibiting certain actions of histamine which are not inhibited by the above-mentioned "antihistamines". The substances of this invention may also be of utility as inhibitors of certain actions of gastrin.

The compounds with which the present invention is concerned may be represented by the following general formula; insofar as tautomerism affects the compounds mentioned in this specification, the numbering of the nucleus has been modified accordingly;

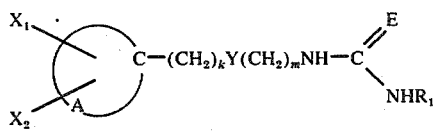

FORMULA I wherein A is such that there is formed together with the carbon atom shown an unsaturated heterocyclic nucleus, which comprises at least one nitrogen and may comprise a further hetero atom such as sulphur and oxygen, said unstaturated heterocyclic nucleus being an imidazole, pyrazole, pyrimidine, prazine, pyridazine, thiazole, isothiazole, oxazole, isoxazole, triazole, triadiazole, benzimidazole or 5,6,7,8-tetrahydroimidazo[1,5-a]pyridine ring; $X_1$ is hydrogen, lower alkyl, hydroxyl, triflouromethyl, benzyl, halogen, amino or

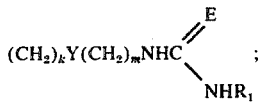

$X_2$ is hydrogen or when $X_1$ is lower alkyl, lower alkyl or halogen; $k$ is 0 to 2 and $m$ is 2 or 3, provided that the sum of $k$ and $m$ is 3 or 4; Y is oxygen, sulphur or NH; E is oxygen or sulphur; and $R_1$ is hydrogen, lower alkyl, benzoyl or di-lower alkylamino-lower alkyl or a pharmaceutically acceptable addition salt thereof. Y is preferably oxygen or sulphur, most advantageously sulphur. Preferably A is such that the nitrogen atom is adjacent to the carbon atom shown and, more preferably, such that it forms with the said carbon atom an imidazole, thiazole or isothiazole ring. Preferably, $X_1$ is hydrogen, methyl, bromo, amino or hydroxyl and $X_2$ is hydrogen. One group of preferred compounds within the present invention is that wherein Y and E are sulphur, $k$ is 1, $m$ is 2 and $R_1$ is methyl. Specific compounds which are found to be particularly useful are N-methyl-N'-[2-(4-imidazolymethylthio)ethyl]thiourea, N-methyl-N'-[2-((5-methyl-4-imidazolyl)methylthio)ethyl]thiourea, N-methyl-N'-[2-((5-bromo-4-imidazolyl)methylthio)ethyl]thiourea, N-methyl-N'-[2-(3-isothiazolylmethylthio)ethyl]thiourea, N-methyl-N'-[2-((4-bromo-3-isothiazolyl)methylthio)ethyl]-thiourea, N-methyl-N'-[2-((1-methyl-2-imidazolyl)methylthio)-ethyl]thiourea, N-methyl-N'-[2-(2-imidazolylmethylthio)-ethyl]thiourea, N-methyl-N'-[2-(2-thiazolymethylthio)ethyl]-thiourea, N-methyl-N'-[2-(5-amino-2-(1,3,4-thiadiazolyl)-methylthio)ethyl]-thiourea, N-methyl-N'-[2-(3-(1,2,4-triazolyl)methylthio)ethyl]thiourea and N-methyl-N'-[3-(2-thiazolylthio)propyl]thiourea.

The compounds with which the present invention is concerned wherein Y is sulphur and $k$ is 1 or 2 may be produced by processes which commence with a substance of the following general formula:

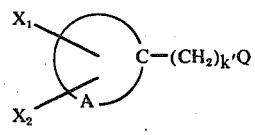

FORMULA II wherein A, $X_1$ and $X_2$ have the same significance as in formula I except that $X_1$ may not be

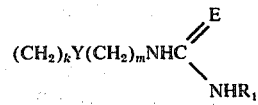

but may additionally be $(CH_2)_k$ Q; $k'$ is 1 or 2 and Q is hydroxyl, halogen or methoxy. In the first stage of these processes, the compound of formula II is reacted with an amino-mercaptan of the following FORMULA III:

wherein $m$ has the same significance as in formula I.

When Q is halogen, this reaction may be carried out under strongly basic conditions, for example in the presence of sodium ethoxide or sodium hydroxide. Since the substance of formula III is a primary amine it may be necessary to protect the amino group, for example by a phthalimido group which may subsequently be removed by acid hydrolysis or by hydrazinolysis.

When Q is hydroxyl or halogen it is found that the reaction will take place under acidic conditions e.g. in the presence of a halogen acid such as 48% aqueous hydrogen bromide, or a halogen acid in the presence of glacial acetic acid. When Q is methoxy, the reaction will also take place in the presence of 48% hydrogen bromide.

When $k$ is zero, the corresponding first stage of the reaction is between a nucleus directly substituted with a thiol or a thione and, under acidic conditions, 3-aminopropanol or, under alkaline conditions, a 3-halopropylamine, the amino group being protected if required in the latter case, e.g. by a phthalimido group which may be subsequently removed by acid hydrolysis or by treatment with hydrazine.

The product produced by these processes is of the following formula IV, and may, of course, be in the form of the acid addition salt:

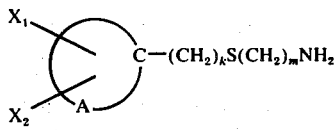

FORMULA IV wherein $X_1$ has the same significance as in formula II and A, $X_2$, $k$ and $m$ have the same significance as in formula I. The free base of formula IV may be obtained from the acid addition salt by treatment with an appropriate base e.g. an alkali metal alkoxide such as sodium ethoxide or an inorganic base such as potassium carbonate.

The compounds of formula I, where $R_1$ is hydrogen, Y is sulphur and E is sulphur may be prepared from an amine of formula IV by reaction with an acyl isothiocyanate such as benzoyl isothiocyanate in an appropriate solvent such as chloroform. Alkaline hydrolysis of these compounds, e.g. the benzoyl derivatives where $R_1$ is $C_6H_5CO$, with a reagent such as aqueous potassium hydroxide or aqueous potassium carbonate yields the compounds of formula I wherein $R_1$ is hydrogen and Y and E are sulphur.

Compounds of formula I wherein $R_1$ is hydrogen, Y is sulphur and E is sulphur may alternatively be prepared directly from the amine of formula IV by reaction at elevated temperature with the thiocyanate of ammonium or of a metal such as sodium or potassium.

The compounds of formula I where $R_1$ is lower alkyl or dialkylaminoalkyl, Y is sulphur and E is sulphur may be prepared from the amine of formula IV by reaction with an isothiocyanic ester of formula $R_1-N=C=S$ in an appropriate solvent such as chloroform, ethanol, isopropanol, acetonitrile or water.

Alternatively the amine of formula IV may be converted by reaction with carbon disulphide to the dithiocarbamic acid of the formula:

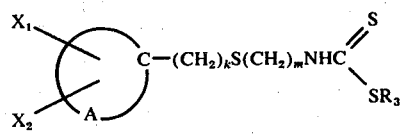

FORMULA V wherein A, $X_1$, $X_2$, $k$ and $m$ have the same significance as in formula IV and $R_3$ is hydrogen, and then methylated to yield the compound of formula V wherein $R_3$ is methyl. Finally, reaction of this methyl ester with an amine of formula $R_1NH_2$, wherein $R_1$ is lower alkyl, yields the required compound.

In the case of compounds of formula I wherein Y is oxygen, the process for their production commences with a compound of formual VI (which may itself be formed by treatment with thionyl halide of the corresponding alcohol resulting from the reaction of a haloakyl heterocyclic compound with the sodium salt of a diol)

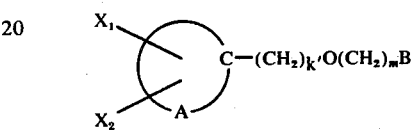

FORMULA VI wherein A, $X_1$, $X_2$ and $m$ have the same significance as in formula I, $k'$ is 1 or 2, $k' + m$ is 3 or 4 and B is halogen. This compound may be reacted with an alkali metal azide and the resulting product reduced, e.g. by hydrogenation over a platinum dioxide catalyst, to yield an amine of formula VII in which $k$ is 1 or 2 and wherein A, $X_1$, $X_2$ and $m$ have the same significance as in formula I.

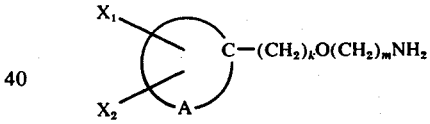

FORMULA VII

The amines of formula VII in which $k$ is zero are prepared by reacting a halo-heterocycle under strongly basic conditions with 1,3-dihydroxypropane, converting the resultant 3-hydroxypropoxy compound with thionyl chloride to the 3-chloropropoxy compound which on reaction with sodium azide and reduction of the product yields the required amine.

The compounds of formula VII may be converted to the compounds of formula I wherein Y is oxygen and E is sulphur by methods analogous to those described hereinabove for the conversion of the compounds of formula IV to those of formula I wherein both Y and E are sulphur.

The compounds of formula I wherein Y is NH and E is sulphur are similarly formed from a compound of formula VIII

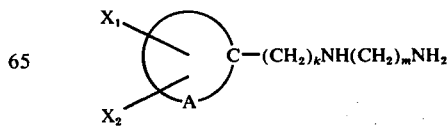

FORMULA VIII
-continued wherein the amino group in the alkylene chain may be protected when $k$ is 1 or 2 and optionally the terminal amino group may also be protected and A, $X_1$, $X_2$, $k$ and $m$ have the same significance as in formula I, except that $X_1$ may not be

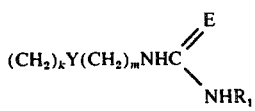

but may additionally be $(CH_2)_kY(CH_2)_mNH_2$.

The intermediates of formula VIII are prepared by a process which commences with a substance of the following general formula:

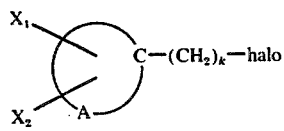

FORMULA IX wherein A, $X_1$, $X_2$ and $k$ have the same significance as in formual I, except that $X_1$ may not be

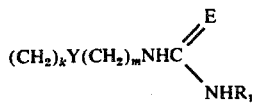

but may additionally be $(CH_2)_k$—halo. In this process, a compound of formula IX is reacted with a diamine of the following FORMULA X:

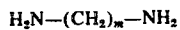

wherein $m$ has the same significance as in formula I. This reaction may be carried out under strongly basic conditions, for example in the presence of sodium ethoxide or sodium hydroxide or in an anhydrous solvent such as dimethylformamide in the presence of sodium hydride. When $k$ is 1 or 2 in formual IX, one of the amino groups of the diamine of formula X may be protected by a group which will be stable under the conditions of the reaction, for example a trifluoroacetyl or a formyl protecting group may be used when the reaction is carried out under anhydrous conditions. When the amino group in the alkylene chain in the resultant intermediate is protected for the process to prepare compounds of this invention, which should then also be carried out under anhydrous conditions, the N-protecting group is finally removed e.g. by treatment with dilute hydrochloric acid.

Alternatively, when $k$ is 0 the appropriate amino heterocyclic compound may be used as the starting material and reacted with a halophthalimido compound of the following FORMULA XI:

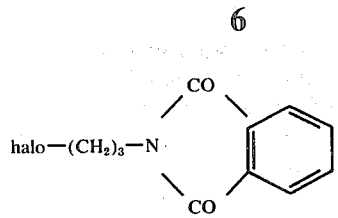

Hydrolysis or hydrazinolysis of the product of this reaction yields the compound of formula VIII wherein $k$ is 0 and $m$ is 3.

Compounds of formula I wherein E is oxygen may be formed from the amines of formula IV, formula VII or formula VIII by treatment thereof with an isocyanate of formula $R_1NCO$ wherein $R_1$ is lower alkyl, benzoyl or dialkylaminoalkyl. The compounds of formula I wherein E is oxygen and $R_1$ is hydrogen may be obtained by reaction of the said amines with sodium or potassium cyanate.

As stated above, when Y is NH any N-protecting group on the NH may be removed, e.g. in the case of N-formyl or N-trifluoroacetyl groups by dilute acid treatment. If no N-protecting groups have been used, a mixture of the desired product of formula I and the corresponding bis-thiourea or bis-urea may be formed from which the former can be separated e.g. by chromatography.

As stated above, the compounds represented by formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane, at doses of from 0.5 to 256 micromoles per kilogram intravenously. Similarly, the action of these compounds is demonstrated by their antagonism to the effects of histamine on other tissues which, according to the above-mentioned paper of Ash & Schild, are not H-1 receptors. Examples of such tissues are perfused isolated guinea-pig heart, isolated guinea-pig right artium and isolated rat uterus. The compounds of the invention have also been found to inhibit the secretion of gastric acid stimulated by pentagastrin or by food. In addition to the above the compounds of the invention also show anti-inflammatory activity in conventional tests such as the rat paw oedema test at doses of about 500 micromoles/kg. subcutaneously.

The level of activity found for the compositions comprising the compounds of the present invention is illustrated by the effective dose range in the anaesthetised rat, as mentioned above of from 0.5 to 256 micromoles per kilogram, given intravenously.

Dose determination studies have been carried out in patients with peptic ulceration who have been shown to have high basal gastric acid secretion. Forty patients have been studied and the results indicate that an oral dose of 200 mg. of metiamide, that is N-methyl-N'-[2-((5-methyl-4-imidazolyl)methylthio)ethyl]thiourea, gives rise in general to plasma levels which are associated with inhibition of gastric acid and pepsin secretion. Twenty-two patients with peptic ulcers who have high levels of basal gastric acid secretion have completed an open pilot study of continuous medication with metiamide (usually 200 mg. q.i.d. orally) for four weeks or more. Many patients have reported complete relief or significant clinical improvement in ulcer pain during metiamide therapy, often such relief occurring within the first few days of the start of treatment. These early reports leave little doubt that metiamide is effective in causing subjective relief of ulcer symptoms.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredient will preferably be administered in equal doses one to four times per day. The daily dosage regimen will preferably be from about 150 mg. to about 1000 mg., most preferably from about 400 mg. to about 800 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric, hydrobromic, hydriodic, sulphuric and maleic acids.

Other pharmacologically active compounds may in certain cases be included in the composition. Advantageously the composition will be made up in a dosage unit form appropriate to the desired mode of administration, for example as a tablet, capsule, injectable solution or, when used as an anti-inflammatory agent, as a cream for topical administration.

The invention is illustrated but in no way limited by the following examples.

Compounds of formula I wherein A is such that there is formed together with the carbon atom shown a five membered unsaturated heteocyclic ring having two nitrogen atoms and three carbon atoms, said unsaturated heterocyclic ring being imidazole or pyrazole, and Y is oxygen or sulphur (sulphur is preferred) are exemplified by the following examples.

EXAMPLE 1

N-Methyl-N'-[2-(4-imidazolylmethylthio)ethyl]thiourea i. (a) A solution of 4(5)-hydroxymethylimidazole hydrochloride (67 g.) and cysteamine hydrochloride (56.8 g.) in aqueous hydrobromic acid (1 liter, 48%) was heated under reflux overnight. After cooling, the solution was evaporated to dryness and the residual solid washed with ethanol/water to give 4(5)-[(2-aminoethyl)thiomethyl]imidazole dihydrobromide (156 g.), m.p. 178°–179°.

b. Phthalimidoethanethiol (2 g.) was added portionwise with stirring to a solution of sodium ethoxide (prepared from 0.23 g. of sodium) in ethanol (20 ml.) at 0° under a nitrogen atmosphere. After stirring at 0° for a further 2.5 hours, the resulting yellow solution was cooled with an ice-salt bath and a solution of 4(5)-chloromethylimidazole hydrochloride (0.76 g.) in ethanol (5 ml.) was added dropwise over 10 minutes. After addition the mixture was stirred at room temperature overnight, then acidified with ethanolic hydrogen chloride and evaporated to dryness. Addition of water precipitated unreacted phthalimidoethanethiol (0.6 g.) which was removed by filtration. The filtrate was concentrated and basified with aqueous sodium bicarbonate solution to furnish a white precipitate which, on recrystallisation from aqueous ethanol, gave 4(5)-[(2-phthalimidoethyl)thiomethyl]imidazole (0.75 g.) m.p. 136°–137°. A stirred mixture of this phthalimido derivative (0.62 g.) in aqueous hydrobromic acid (40 ml. 18%) was heated under reflux overnight. After cooling to 0°, the resulting clear solution was filtered and the filtrate evaporated to dryness. Recrystallisation of the residue from ethanol gave 4(5)-[(2-aminoethyl)thiomethyl]imidazole dihydrobromide (0.52 g.), m.p. 178°–179°.

c. A suspension of cysteamine hydrochloride (118.8 g.) in ethanol (200 ml., dried over molecular sieves) was added portionwise at 0° to a solution of sodium ethoxide (prepared from 48 g. of sodium) in ethanol (1 liter) under a nitrogen atmosphere. After stirring at 0°, for a further 2 hours, a solution of 4(5)-chloromethylimidazole hydrochloride (80 g.) in ethanol (400 ml.) was added dropwise over 45 minutes while the temperature was maintained at −1°±2°. After addition, the mixture was stirred at room temperature overnight, filtered, and the filtrate acidified with concentrated hydrochloric acid. The solution was then evaporated to dryness, the residue dissolved in ethanol (1 liter) and a solution of excess picric acid in hot ethanol added. The resulting crude picrate was dissolved in water (2.7 liters) and, after decantation from an insoluble oil, the solution was left to cool to give 4(5)-[(2-aminoethyl)-thiomethyl]imidazole dipricate, m.p. 194°–195°. Treatment of this picrate with aqueous hydrobromic acid followed by extraction with toluene gave the dihydrobromide, m.p. 178°–179°, after evaporation to dryness and recrystallisation of the crude residue from ethanol.

(ii) A solution of 4(5)-[(2-aminoethyl)thiomethyl]imidazole dihydrobromide (10 g.) in water (25 ml.) was basified to pH 11 by the addition of a solution of potassium carbonate (8.7 g.) in water (25 ml.). The resulting solution was evaporated to dryness, extracted with isopropyl alcohol and the final traces of water removed by azeotroping with isopropyl alcohol. The residual amine was extracted from the inorganic material with isopropyl alcohol, the extracts concentrated to about 70 ml. and a solution of methyl isothiocyanate (2.3 g.) in isopropyl alcohol (5 ml.) added. The reaction mixture was then heated under reflux for 1.5 hours and, after cooling, evaporated to dryness. The residual oil was dissolved in acetone, the solution filtered to remove traces of inorganic material, and the filtrate concentrated to give N-methyl-N'-[2-(4-imidazolylmethylthio)-ethyl]thiourea (4.1 g.), m.p. 96°–98°. A sample, recrystallised from acetone, had m.p. 98°–99°. (Found: C, 41.8; H, 6.4; N, 24.4; S, 27.6. $C_8H_{14}N_4S_2$ requires: C, 41.7; H, 6.1; N, 24.3; S, 27.8).

EXAMPLE 2

N-Methyl-N'-[2-((5-methyl-4-imidazolyl)methylthio)ethyl]thiourea i. (a) A solution of 4-hydroxymethyl-5-methylimidazole hydrochloride (30.0 g.) and cysteamine hydrochloride (23.0 g.) in acetic acid (200 ml.) was heated under reflux for 10 hours. Following cooling to 15°–20°, the solid which crystallised was collected and washed with isopropyl alcohol to give 4-methyl-5-[(2-aminoethyl)thiomethyl]imidazole dihydrochloride (45.5 g.), m.p. 189°–192°.

b. A solution of 4-hydroxymethyl-5-methylimidazole hydrochloride (30.0 g.) and cysteamine hydrochloride (23.0 g.) in concentrated aqueous hydrochloric acid (450 ml.) was heated under reflux for 17 hours. Concentration followed by re-evaporation with water afforded a residue which was dissolved in isopropyl alcohol, concentrated to low bulk and cooled to afford 4-methyl-5-[(2-aminoethyl)thiomethyl]-imidazole dihydrochloride (40.6 g.), m.p. 185°–191°.

c. A mixture of 4-hydroxymethyl-5-methylimidazole hydrochloride (15.0 g.), cysteamine hydrochloride (11.5 g.) and a solution of hydrogen bromide in acetic acid (48%, 225 ml.) was heated under reflux for 7 hours. Cooling afforded 4-methyl-5-[2-aminoethyl)thiomethyl]imidazole dihydrobromide (21.6 g.), m.p. 208°–211°.

ii. Potassium carbonate (7.75 g.) was added to a solution of 4-methyl-5-[(2-aminoethyl)thiomethyl]imidazole dihydrochloride (14.6 g.) in water (120 ml.). The solution was stored at room temperature for 15 minutes and methyl isothiocyanate (5.15 g.) was added. After heating under reflux for 30 minutes, the solution was slowly cooled to 5°.

The product (13.1 g.) was collected and recrystallised from water to give N-methyl-N'-[2-((5-methyl-4-imidazolyl)methylthio)ethyl]thiourea, m.p. 150°–152°. (Found: C, 44.5; H, 6.7; N, 23.0; S, 26.2. $C_9H_{16}N_4S_2$ requires: C, 44.2; H, 6.6; N, 22.9; S, 26.2).

EXAMPLES 3–13

By two-stage processes essentially similar to those described in Example 1 (i) and (ii) were produced thiourea compounds of the formula:

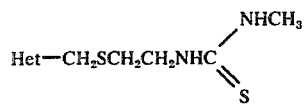

wherein Het has the significance as set out in the following table I. The solvent from which the product was crystallised and the melting point and elemental analysis data of the product are also set out in the table together with the melting point of the corresponding intermediate amine salt of formula:

wherein W is a picrate or bromide anion as indicated in the table.

The starting materials of formula:

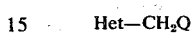

wherein Q is hydroxyl, halogen or methoxy are all known compounds with the exception of those used in Examples 3, 4 and 5 the preparation of which is described hereinafter. In each case, the starting material was reacted with cysteamine hydrochloride in aqueous hydrobromic acid as described in Example 1 (i) (a). Where necessary, the resultant amine was purified by conversion to the picrate followed by treatment with hydrochloric or hydrobromic acid and removal of picric acid, thus yielding the corresponding hydrochloride or hydrobromide (as described in Example 1 (i) (c)).

Conversion of this hydrochloride or hydrobromide into the free base by the addition of potassium carbonate followed by concentration and extraction with isopropanol or ether/ethanol (3:1) yielded an extract which was reacted with methyl isothiocyanate in an appropriate solvent under conditions similar to those described in Example 1 (ii). The resultant thiourea products, where crystallisable, were recrystallised from a solvent as indicated in table 1.

Preparation of starting materials for Examples 3, 4 and 5 a. 5-Ethyl-4-hydroxymethylimidazole hydrochloride (Example 3)

Sulphuryl chloride (286 g.) was added dropwise to a solution of ethyl 3-oxopentanoate (300 g.) in chloroform (250 ml.) at 10°–15°. Following addition the mixture was stirred overnight at room temperature, heated under reflux for 0.5 hours and cooled. After washing with water, sodium bicarbonate and water, the solution was dried (sodium sulphate), concentrated, and fractionated to yield ethyl 2-chloro-3-oxopentanoate, b.p. 94°–96°/14 mm.

A mixture of ethyl 2-chloro-3-oxopentanoate (178 g.), freshly distilled formamide (450 g.) and water (38 ml.) was heated at 140°–148° and then cooled and added to dilute hydrochloric acid. After decanting from insoluble material, the solution was basified with ammonium hydroxide to give a solid which, following recrystallisation from aqueous ethanol and ethanol-acetate, yielded 5-ethyl-4-carbethoxyimidazole (29 g.) m.p. 170°–172°. This ester (14.0 g.) was reduced with lithium aluminium hydride (4.6 g.) in tetrahydrofuran and then treated with hydrogen chloride to give 4-ethyl-5-hydroxymethylimidazole hydrochloride (10.6 g.) m.p. 141°–142° (from isopropyl alcohol-ether).

TABLE 1

Product: N-methyl-N'-[2-((* * *)methylthio)ethyl]thiourea

| Ex. No. | Het (* * *) | W | Intermediate amine salt m.p. (°C) | Recryst. from | Product m.p. (°C) | Molecular Formula | Found C | Found H | Found N | Found S | Required C | Required H | Required N | Required S |
|---|---|---|---|---|---|---|---|---|---|---|---|---|---|---|
| 3 | C₂H₅ (5-ethyl-4-imidazolyl) 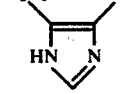 | bromide | — | aqueous ethanol | 187–189 | C₁₀H₁₈N₄S₂ · 2 Picrolonate | 46.3 | 5.0 | 21.2 | 12.1 | 46.0 | 5.1 | 21.4 | 12.3 |
| 4 | i-C₃H₇ (5-isopropyl-4-imidazolyl) 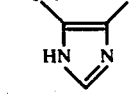 | picrate | 170–172.5 | isopropyl acetate/ether | 486–89 | C₁₁H₂₀N₄S₂ | 48.5 | 7.6 | 20.8 | 23.6 | 48.5 | 7.4 | 20.6 | 23.5 |
| 5 | PhCH₂ (5-benzyl-4-imidazolyl) 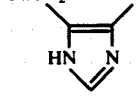 | bromide | — | aqueous ethanol | 131–133 | C₁₅H₂₀N₄S₂ | 56.0 | 6.2 | 17.3 | 20.0 | 56.2 | 6.3 | 17.5 | 20.0 |
| 6 | Br (5-bromo-4-imidazolyl) 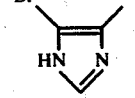 | bromide | 180–181 | aceto-nitrile | 152–153 | C₈H₁₃BrN₄S₂ | 31.1 | 4.4 | 18.1 | 20.4 | 31.1 | 4.2 | 18.1 | 20.7 |
| 7 | (2-methyl-4-imidazolyl)  | bromide | 181–2 | water | 119–122 | C₉H₁₆N₄S₂ | 44.0 | 6.6 | 22.7 | 25.9 | 44.2 | 6.6 | 22.9 | 26.2 |
| 8 | (1-methyl-4-imidazolyl) 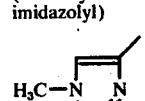 | bromide | 196–8 | methyl methyl ketone | 114–115 | C₉H₁₆N₄S₂ | 44.5 | 6.7 | 22.8 | 25.7 | 44.2 | 6.6 | 22.9 | 26.2 |
| 9 | (2-imidazolyl) 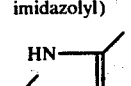 | bromide | 195–197 | ethyl acetate/petroleum ether | 76–78 | C₈H₁₄N₄S₂ | 41.8 | 6.1 | 24.3 | 27.9 | 41.7 | 6.1 | 24.3 | 27.8 |
| 10 | CH₃ (1-methyl-2-imidazolyl) 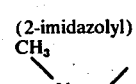 | picrate | 172–174 | isopropyl acetate/ethanol | 114–116 | C₉H₁₆N₄S₂ | 44.5 | 6.8 | 23.0 | 26.2 | 44.2 | 6.6 | 23.0 | 26.2 |
| 11 | H₃C (1,5-dimethyl-2-imidazolyl) 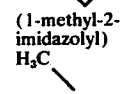 | bromide | — | isopropyl acetate | 105–107 | C₁₀H₁₈N₄S₂ | 46.4 | 6.8 | 21.6 | 24.8 | 46.5 | 7.0 | 21.7 | 24.8 |
| 12 | H₃C (5-chloro-1-methyl-2-imidazolyl) 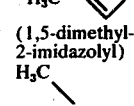 | bromide | — | water | 96–98 | C₉H₁₅ClN₄S₂ | 38.6 | 5.3 | 19.9 | 22.6 | 38.8 | 5.4 | 20.1 | 23.0 |

TABLE 1-continued

| | Intermediate amine salt | | | | Product: N-methyl-N'-[2-((* * *)methylthio)ethyl]thiourea | | | | | | | | |
|---|---|---|---|---|---|---|---|---|---|---|---|---|---|
| | | | | | | Elemental Analysis | | | | | | | |
| Ex. | Het | | m.p. | Recryst. | m.p. | Molecular | Found | | | | Required | | | |
| No. | (* * *) | W | (° C) | from | (° C) | Formula | C | H | N | S | C | H | N | S |
| 13 | 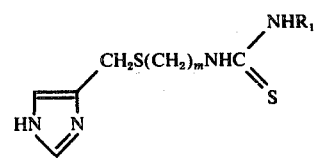 (3-pyrazolyl) | bromide | 153–154 | — | — | C₈H₁₄N₄S₂ | 41.9 | 6.1 | 23.7 | | 41.7 | 6.1 | 24.3 | | b. 4-Isopropyl-5-hydroxymethylimidazole hydrochloride (Example 4)

A solution of sodium nitrite (43.8 g.) in water (92 ml.) was added dropwise, with stirring, to a solution of ethyl isobutyrylacetate (100.3 g.) in acetic acid (80 ml.) at 0°. After stirring at 0° for 30 minutes at room temperature for 3 hours, water (100 ml.) was added and the mixture extracted with ether. The extracts were washed with water, saturated sodium bicarbonate solution and water. After drying (CaSO₄), the solution was evaporated to give ethyl 2-oximino-4-methyl-3-oxopentanoate (112 g.) as a crude oil.

A solution of this oximinoketone (219 g.) in ethanol (280 ml.) was added to a suspension of pre-reduced palladised charcoal (10 g., 10%) in ethanol (1 lit.) and saturated ethanolic hydrogen chloride (512 ml.) and the mixture hydrogenated at room temperature and pressure until the theoretical amount of hydrogen was taken up. The mixture was filtered, and filtrate concentrated and ethyl acetate added to give ethyl 2-amino-4-methyl-3-oxopentanoate hydrochloride (230.6 g.) m.p. 129°–131° (dec.). This aminoketone (50.5 g.) was dissolved in redistilled formamide (180 ml.) and the solution heated at 120° for 2 hours, 130° for 1 hour, and finally at 140° for 2 hours. After cooling, the mixture was filtered and the crystalline product washed with water to give ethyl 4-isopropyl-5-carbethoxy-imidazole (22 g.) m.p. 177°–178°.

This ester (108 g.) was placed in a soxhlet and reduced with lithium aluminium hydride (34.5 g.) in tetrahydrofuran to give 4-hydroxymethyl-5-isopropylimidazole (62.3 g.) m.p. 121°–123°.

c. 4-Benzyl-5-hydroxymethylimidazole hydrochloride (Example 5)

Reaction of ethyl 3-oxo-4-phenylbutyrate (10.3 g.) with sodium nitrite followed by reduction of the crude ethyl 2-oximino-3-oxo-4-phenylbutyrate (10.8 g.) as described in the previous section, (b), gave ethyl 2-amino-3-oxo-4-phenylbutyrate hydrochloride (8.5 g.) m.p. 150°–153°. An analytical sample, recrystallised from ethanol/ethyl acetate, had m.p. 154°–155°.

Reaction of this aminoketone (160 g.) with formamide (480 ml.) by the method described in the previous section, (b), gave 4-benzyl-5-carbethoxyimidazole (75 g.) m.p. 168.5°–169.5°. Reduction of this ester (30 g.) with lithium aluminium hydride (6.4 g.) in tetrahydrofuran (600 ml.), followed by addition of water, filtration and acidification of the filtrate with ethanolic hydrogen chloride, gave 4-benzyl-5-hydroxymethylimidazole hydrochloride (22.9 g.), m.p. 149°–151°, after concentration and addition of ethyl acetate.

EXAMPLES 14–16

Two stage processes as described in Examples 3–13 were used for the production of compounds of the following formula:

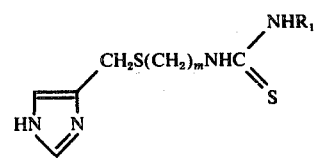

wherein $R_1$ has the significance as set out in Table 2. In each case the intermediate amine was of the formula:

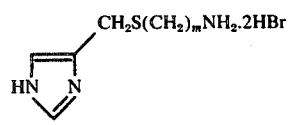

Table 2 shows the values for $m$ and $R_1$ and recrystallisation solvent, melting point and elemental analysis for each product.

TABLE 2

| | | | | Product: N-(* * *)-N'-(ω-(4-imidazolylmethylthio)* *)thiourea | | | | | | | | | | |
|---|---|---|---|---|---|---|---|---|---|---|---|---|---|---|
| Ex. | | | Recrystallised | m.p. | Molecular | Elemental Analysis | | | | | | | Nomenclature | | |
| | | | | | | Found | | | | Required | | | | | |
| No. | m | $R_1$ | from | (° C) | Formula | C | H | N | S | C | H | N | S | *** | ω | *** |
| 14 | 3 | CH₃ | water | 118–120 | C₉H₁₆N₄S₂ | 44.0 | 6.7 | 22.9 | 25.7 | 44.2 | 6.6 | 22.9 | 26.2 | methyl | 3 | propyl |
| 15 | 2 | C₂H₅ | water | 128–129 | C₉H₁₆N₄S₂ | 44.2 | 6.9 | 23.2 | 26.4 | 44.2 | 6.6 | 22.9 | 26.2 | ethyl | 2 | ethyl |
| 16 | 2 | CH₂CH₂-N(CH₃)₂ | isopropyl acetate/ether | 97–99.5 | C₁₁H₂₁N₅S₂ | 46.2 | 7.6 | 24.7 | 22.2 | 46.0 | 7.4 | 24.4 | 22.3 | 2-dimethyl-aminoethyl | 2 | ethyl |

Using the process of Example 14 from 4-methyl-5-[(3-aminopropyl) thiomethyl]imidazole dihydrobromide, m.p. 200.5°–202.5°, the product is N-methyl-N'-[3-((4-methyl-5-imidazolyl)methylthio)propyl]thiourea, m.p. 104.5°–105.5° (from methyl ethyl ketone). (Found: C, 46.6; H, 7.0; N, 21.7; S, 24.6. $C_{10}H_{18}N_4S_2$ requires: C, 46.5; H, 7.0; N, 21.7; S, 24.8).

Using the process of Example 15, commencing from 4-methyl-5-[(2-aminoethyl)thiomethyl]imidazole, the product is N-ethyl-N'-[2-(4-methyl-5-imidazolyl)methylthio)ethyl]-thiourea, m.p. 140°–141°. (Found: C, 46.5; H; 7.1; N, 21.7; S, 25.1. $C_{10}H_{18}N_4S_2$ requires: C, 46.5; H, 7.0; N, 21.7; S, 24.8).

EXAMPLE 17

N-Methyl-N'-[2-(2-(4-imidazolyl)ethyl)thioethyl]-thiourea dihydroiodide i. A solution of 4(5)-(2-chloroethyl)imidazole hydrochloride (13.6 g.) and cysteamine hydrochloride (9.3 g.) in distilled water (100 ml.) was added over 30 minutes to a stirred solution of potassium hydroxide (15.8 g., 85%) in water (40 ml.) at room temperature under a nitrogen atmosphere. After addition the solution was heated for 4 hours at 50°. From time to time it was necessary to add a few drops of potassium hydroxide solution to prevent the pH of the reaction mixture falling below 11. The reaction mixture was then acidified with 2N hydrochloric acid, evaporated to dryness under reduced pressure and the final traces of water removed by azeotroping with n-propanol. The residue was extracted several times with isopropyl alcohol and the combined extracts added to a hot solution of picric acid in isopropyl alcohol. On cooling, this gave 4(5)-[2-(2-aminoethyl)thioethyl]imidazole dipicrate (42.3 g.) m.p. 225°–226°.

ii. This dipicrate was converted to the dihydrochloride by addition of concentrated hydrochloric acid (200 ml.) followed by extraction with toluene (5×50 ml.). The aqueous solution was evaporated to dryness, the residue dissolved in water and the solution basified by the addition of aqueous potassium carbonate solution. This mixture was then evaporated to dryness and the residue extracted with n-propanol to give the crude base of 4(5)-[2-(2-aminoethyl)-thioethyl]imidazole on removal of the n-propanol. A solution of this base (3.3 g.) and methyl isothiocyanate (1.9 g.) in ethanol (15 ml.) was heated under reflux for 30 minutes. After cooling the solution was evaporated to dryness and the residue chromatographed on silica gel. Elution with ethyl acetate/methanol (3:2) and evaporation of the appropriate middle fractions gave an oily residue, which was acidified with aqueous hydriodic acid (64%). Decantation several times with ether gave a yellow precipitate which, on washing with acetonitrile and then ether, gave N-methyl-N'-[2-(2-(4-imidazolyl)ethyl)thioethyl]thiourea hydroiodide, m.p. 143°–145°, as an off-white solid. (Found: C, 21.6; H, 3.7; N, 11.1; S, 12.9; I, 50.7. $C_9H_{16}N_4S_2\cdot 2HI$ requires: C, 21.6; H, 3.6; N, 11.2; S, 12.8; I, 50.7).

EXAMPLE 18

N-[2-(4-Imidazolylmethylthio)ethyl]thiourea i. A solution of 4(5)-[(2-aminoethyl)thiomethyl]imidazole (6.0 g.) and benzoyl isothiocyanate (6.0 g.) in chloroform (150 ml.) was heated under reflux for one hour. Concentration followed by recrystallisation from ethyl acetate-isopropyl acetate afforded N-benzoyl-N'-[2-(4-imidazolylmethylthio)-ethyl]thiourea (7.5 g.). An analytically pure sample (from aqueous isopropyl alcohol) has m.p. 126°–128°.

ii. The benzoyl thiourea (6.0 g.) was added to a solution of potassium carbonate (1.4 g.) in water (80 ml.), at 60°. The solution was maintained at this temperature for one hour, concentrated to low bulk and acidified with hydrochloric acid. Benzoic acid was removed by filtration and the filtrate was basified with potassium carbonate and concentrated under reduced pressure. Following extraction with isopropyl alcohol and concentration, the product was crystallised from isopropyl acetate. Recrystallisation from water gave N-[2-(4-imidazolymethylthio)ethyl]thiourea (2.5 g.) m.p. 135°–137°. (Found C, 38.9; H, 5.5; N, 26.1; S, 29.6. $C_7H_{12}N_4S_2$ requires: C, 38.9; H, 5.6; N; 25.9; S, 29.6).

EXAMPLE 19

N-[(2-(4-methyl-5-imidazolyl)methylthio)ethyl]thiourea a. The reaction of 4-methyl-5-((2-amino ethyl)thiomethyl)-imidazole (5.0 g.) and benzoyl isothiocyanate (23.8 g.) by the procedure described in Example 18 (i) afforded N-benzoyl-N'-[(2-(4-methyl-5-imidazolyl)methylthio)ethyl]thiourea (24 g.), m.p. 138°–140° (from isopropyl alcohol-ethylacetate-ether). An analytically pure sample obtained by recrystallisation from aqueous isopropyl alcohol had m.p. 165°–166°.

b. The crude benzoyl thiourea (22 g.) was hydrolysed with potassium carbonate by the procedure described in Example 18 (ii) to afford N-[2-(4-methyl-5-imidazolyl)methylthio)ethyl]-thiourea (7.5 g.). Further recrystallisation from water, followed by isopropyl alcohol-ether gave the pure product (3.8 g.) m.p. 110°–112°. (Found: C, 41.9; H, 6.3; N, 24.5; S, 28.0 $C_8H_{14}N_4S_2$ requires: C, 41.7; H, 6.1; N, 24.3; S, 27.8).

EXAMPLE 20

4,5-bis-[2-(N-Methylthioureido)ethylthiomethyl-]imidazole i. The reaction of 4,5-di(hydroxymethyl)imidazole hydrochloride (1.6 g.) with cysteamine hydrochloride (2.2 g.) by the procedure described in Example 1 (i) (a) afforded 4,5-bis-((2-aminoethyl)thiomethyl)imidazole trihydrobromide (3.8 g.), m.p. 233°–236°.

ii. The reaction of 4,5-bis-((2-aminoethyl)thiomethyl)-imidazole (1.2 g.) with methyl isothiocyanate (1.5 g.) by the procedure described in Example 1 (ii) afforded 4,5-bis-[2-(N-methylthioureido)ethylthiomethyl]imidazole (1.1 g.) m.p. 154°–155° (from isopropyl alcohol - isopropyl acetate) (Found: C, 39.8; H, 6.2; N, 21.5; S, 32.5. $C_{13}H_{24}N_6S_4$ requires: C, 39.8; H, 6.2; N, 21.4; S, 32.7).

EXAMPLE 21

N-Methyl-N'-[3-(2-imidazolythio)propyl]thiourea i. A solution of 2-mercaptoimidazole (2 g.) and 3-aminopropanol (1.14 ml.) in hydrobromic acid (48%, 25 ml.) was heated under reflux for 25 hours. The reaction mixture was evaporated to dryness and the oily residual solid recystallised twice from ethanol/ether to give 2-(3-aminopropyl-mercapto)imidazole dihydrobromide (3.55 g.) m.p. 160°–162°.

(ii) This amine dihydrobromide (7 g.) was converted to the free base and reacted with methyl isothiocyanate (1.75 g.), by the method described in Example 1 (ii), to give a crude yellow solid after evaporation of the reaction mixture. This crude product was washed with acetone/isopropyl acetate (1:1) and recrystallised from water to give N-methyl-N'-[3-(2-imidazolylthio)-propyl]thiourea (3.46 g.) m.p. 139°–141°. (Found: C, 41.5; H, 6.1; N, 24.1; S, 27.7. $C_8H_{14}N_4S_2$ requires: C, 41.7; H, 6.1; N, 24.3; S, 27.8).

EXAMPLE 22

The process described in Example 21 (i) was used to prepare 2-(3-aminopropylthio)-1-methylimidazole dihydrobromide, m.p. 164°–166°.

This amine dihydrobromide was used in the process of Example 21 (ii) to give a product which was crystallised from water to give N-methyl-N'-[(3-(1-methyl-2-imidazolyl)-thio)propyl]thiourea, m.p. 109°–111°. (Found: C, 44.5; H, 6.5; N, 23.1; S, 26.3. $C_9H_{16}N_4S_2$ requires: C, 44.2; H, 6.6; N, 22.9; S, 26.2).

EXAMPLE 23

N-Methyl-N'-[2-(4-imidazolymethoxy)ethyl]thiourea i. A stirred suspension of 4-(2-chloroethoxymethyl)imidazole hydrochloride (14.7 g.) and sodium azide (9.8 g.) in dry dimethylformamide (103 ml.) was maintained at 95° for 5 hours and then set aside overnight at room temperature. Following dilution with water and filtration, the filtrate was concentrated and the residue purified by chromatography on a dry column of alumina using ethanol. The product was basified with potassium carbonate (6.5 g.) in water (3 ml.) and the anhydrous residue was extracted with isopropyl alcohol (3 × 50 ml.). Concentartion of the extracts afforded 4-(2-azidoethoxymethyl)imidazole (7.2 g.). Hydrogenation of the azido compound (7.2 g.) in isopropyl alcohol (142 ml.) over platinum oxide catalyst (3.0 g.) gave 4-(2-aminoethoxymethyl) imidazole (6.48 g.). A sample of the monopicrate monohydrochloride had m.p. 139°–140° (from nitromethane). (Found: C, 35.4; H, 3.8; N, 20.5; Cl, 8.8. $C_{12}H_{15}ClN_6O_8$ requires: C, 35.4; H, 3.7; N, 20.7; Cl, 8.7).

ii. 4-(2-Aminoethoxymethyl)imidazole (2.24 g.) was caused to react with methyl isothiocyanate (1.21 g.) in isopropyl alcohol (25 ml.) in the usual way. The crude product was purified by chromatography on a column of silica gel with ethyl acetate as eluant and subsequently on a dry column of alumina, using chloroform. The final product was recrystallised from ethyl acetate to give N-methyl-N'-[2-(4-imidazolylmethoxy)ethyl]-thiourea (0.80 g.), m.p. 96°–98°. (Found: C, 44.6; H, 6.5; N, 26.0; S, 14.7. $C_8H_{14}N_4OS$ requires: C, 44.8; H, 6.6; N, 26.2; S, 15.0).

EXAMPLE 24

N-Methyl-N'-[2-((4-methyl-5-imidazolyl)methylthio)ethyl]urea

A mixture of 4-methyl-5-[(2-aminoethyl)thiomethyl]-imidazole (5.1 g.) and methyl isocyanate (2.0 g.) in acetonitrile was heated for 18 hours in a pressure vessel at 100°. After cooling, the solid obtained was collected and recrystallised from isopropyl alcohol-acetonitrile to give N-methyl-N'-[2-((4-methyl-5-imidazolyl)methylthio)ethyl]urea (4.0 g.) m.p. 158°–159°. (Found: C, 47.4; H, 7.1; N, 24.5; S, 14.1. $C_9H_{16}N_4OS$ requires: C, 47.3; H, 7.1; N, 24.5; S, 14.0).

EXAMPLE 25

N-Methyl-N'-[2-(1,4-dimethyl-2-imidazolyl)methylthio)ethyl]-thiourea i. The reaction of 1,4-dimethylimidazole (5.65 g.) with n-butyl lithium followed by treatment with formaldehyde according to the method described for the preparation of 3-hydroxymethyl-5,6,7,8-tetrahydroimidazol[1,5-a]pyridine (used for Example 224) gave 1,4-dimethyl-2-hydroxymethylimidazole (2.71 g.), m.p. 125°–126° (ethyl acetate-petroleum ether).

ii. The reaction of 1,4-dimethyl-2-hydroxymethylimidazole (2.5 g.) with cysteamine hydrochloride (2.5 g.) in aqueous hydrobromic acid by the method described in Example 1 (i) (a) gave 1,4-dimethyl-2-[(2-aminoethyl)thiomethyl]imidazole dihydrobromide (6.2 g.) m.p. 161°–163° (from isopropyl alcohol-methoanol).

iii. The reaction of 1,4-dimethyl-2-[(2-aminoethyl)-thiomethyl]imidazole (derived from the 6.2 g. dihydrobromide) with methyl isothiocyanate (1.34 g.) in ethanol (50 ml.) followed by chromatography on a column of silica gel with ethyl acette-ethanol (9:1) as eluant gave N-methyl-N'-[2-(1,4-dimethyl-2-imidazolyl)methylthio)ethyl]thiourea (2.1 g.). (Found: C, 4.8; H, 6.9; N, 21.5; S, 24.9. $C_{10}H_{18}N_4S_2$ requires: C, 46.5; H, 7.0; N, 21.7; S, 24.8).

EXAMPLE 26

N-Methyl-N'-[2-((4-trifluoromethyl-5-imidazolyl)methylthio)-ethyl]thiourea

A mixture of ethyl 2-chloro-4,4,4-trifluoroacetate (65.7 g.), distilled formamide (135 g.) and water (11 ml.) was heated at 129°–130° for 1.5 hours. After cooling, an equal volume of ice-cold water was added to give 4-trifluoromethyl-5-carbethoxyimidazole, m.p. 184°–186° (from aqueous methanol).

Reduction of the ester (9.4 g.) with lithium aluminium hydride (2.4 g.) in tetrahydrofuran gave 5-hydroxymethyl-4-trifluoromethylimidazole, isolated as its picrate, m.p. 135.5°–137.5° (from aqueous isopropyl alcohol).

The picrate (5.3 g.) was dissolved in 48% aqueous hydrobromic acid and extracted with toluene to remove picric acid. Cysteamine hydrochloride (1.52 g.) was added to the aqueous phase and the acidic solution heated under reflux for 12 hours. Concentration and trituration of the residue with ethanol-ether gave 4-trifluoromethyl-5-[(2-aminoethyl)thiomethyl]imidazole dihydrobromide (3.2 g.), m.p. 179°–182°. Basification followed by treatment with methyl isothiocyanate gave N-methyl-N'-[2-((4-trifluoromethyl-5-imidazolyl)methylthio)ethyl]thiourea.

EXAMPLE 27

N-[(2-(4-methyl-5-imidazolyl)methylthio)ethyl]urea

A solution of 4-methyl-5-[(2-amino-ethyl)thiomethyl]imidazole dihydrobromide (3.33 g.), potassium cyanate (0.81 g.) and potassium carbonate (0.69 g.) in water (30 ml.) was heated at 80°–90° for 3 hours. Concentration under reduced pressure and extraction of the residue with n-propanol gave the crude product which was chromatographed on a column of silica gel with ethyl acetate-ethanol (5:1) as eluant. Recrystallisation from isopropyl alcohol-ether and finally from acetonitrile furnished N-[(2-(4-methyl-5-imidazolyl)- methylthio)ethyl]urea (0.8 g.), m.p. 148°–149°. (Found: C, 44.6; H, 6.5; N, 25.7; S, 15.0. $C_8H_{14}N_4OS$ requires: C, 44.8; H, 6.6; N, 26.1; S, 15.0).

EXAMPLE 28

N-Methyl-N'-[3-(4-imidazolylmethoxy)propyl]thiourea i. Sodium (13.5 g.) was added over 3 hours to propane-1,3-diol (450 ml.) under nitrogen at 70° with stirring. This solution was added over 20 minutes to a stirred solution of 4-chloromethylimidazole hydrochloride (50.0 g.) under nitrogen at 40°–60°. Subsequent heating at 60°–65° for 3 hours followed by overnight cooling, filtration and concentration gave 4-(3-hydroxypropoxy)methylimidazole. Subsequent reaction with thionyl chloride gave 4-(3-chloropropoxy)methylimidazole hydrochloride (38.8 g.).

ii. The reaction of this chloride (36.2 g.) with sodium azide (22.4 g.) in dry dimethylformamide at 90° for 3 hours followed by 'dry-column' chromatography on aluminium with ethanol as eluant gave 4-(3-azidopropoxy)methylimidazole which was further purified by the same method using chloroform as eluant. The azide (2.95 g.) in ethanol (200 ml.) was hydrogenated over platinum oxide catalyst to give 4-(3-aminopropoxy)methylimidazole (2.42 g.).

iii. Reaction of the amine (2.42 g.) with methyl isothiocyanate (1.25 g.) in ethanol at room temperature for 65 hours followed by chromtography of the product on a column of silica gel with ethyl acetate as eluant gave N-methyl-N'-[3-(4-imidazolylmethoxy)propyl]-thiourea (0.49 g.) as a low melting solid.

EXAMPLE 29

N-Methyl-N'-[2-((2-amino-4-imidazolyl)methylthio)ethyl]thiourea

Freshly prepared sodium amalgam (90 g.) is added over 75 minutes to a stirred solution of series ethyl ester dihydrochloride (3.0 g.) in water/ethanol (2:1), the temperature being maintained within the range of from −12° to −10° and the pH at about 2.5 by the addition of 5N hydrochloric acid. After a further 45 minutes the mixture is allowed to warm to 10° and the precipitated free mercury is removed. Canamide is added and the mixture warmed to 50° for 30 minutes, left at 0° for 18 hours and evaporated to dryness. After washing with ether to remove any unchanged cyanamide, the residue is extracted with hot ethanol and heated with hot ethanolic picric acid. Concentration and cooling of the solution gives 2-amino-4-hydroxymethylimidazole picrate.

Reaction of 2-amino-4-hydroxymethylimidazole hydrochloride (which is obtained by treating the picrate salt with hydrochloric acid) with cysteamine hydrochloride and reaction of the resulting 2-amino-4-[(2-aminoethyl)-thiomethyl]imidazole with methyl isothiocyanate by the methods of Example 1 gives N-methyl-N'-[2-((2-amino-4-imidazolyl)methylthio)ethyl]thiourea.

EXAMPLE 30

| Ingredients | Amounts |
|---|---|
| N-Methyl-N'-[2-((5-methyl-4-imidazolyl)methylthio)ethyl]thiourea | 150 mg. |
| Sucrose | 75 mg. |
| Starch | 25 mg. |
| Talc | 5 mg. |
| Stearic acid | 2 mg. |

The ingredients are screened, mixed and filled into a hard gelatin capsule.

EXAMPLE 31

| Ingredients | Amounts |
|---|---|
| N-Methyl-N'-[2-(4-imidazolylmethylthio)-ethyl]thiourea | 200 mg. |
| Lactose | 100 mg. |

The ingredients are screened, mixed and filled into a hard gelatin capsule.

EXAMPLE 32

By the procedure of Example 1, using in place of 4(5)-hydroxymethylimidazole hydrochloride, the hydrochloride salts of the following compounds:
  5-methyl-3-hydroxymethylpyrazole
  3,5-dimethyl-4-hydroxymethylpyrazole
  5-hydroxy-3-hydroxymethylpyrazole
  3,4-di(hydroxymethyl)pyrazole
the following products are obtained, respectively:
  N-methyl-N'-[2-((5-methyl-3-pyrazolyl)methylthio)ethyl]-thiourea
  N-methyl-N'-[2-((3,5-dimethyl-4-pyrazolyl)methylthio)-ethyl]thiourea
  N-methyl-N'-[2-((5-hydroxy-3-pyrazolyl)methylthio)ethyl]-thiourea
  3,4-bis-[2-(N-methylthioureido)ethylthiomethyl]-pyrazole.

EXAMPLE 33

N-Methyl-N'-[2-((4-hydroxy-3-pyrazolyl)methylthio)ethyl]thiourea

4-Hydroxy-3-pyrazolecarboxylic acid is converted to the ethyl ester and the ester is reduced with lithium aluminium hydride in tetrahydrofuran to give 4-hydroxy-3-hydroxymethylpyrazole, which is treated with aqueous hydrochloric acid to give the hydrochloride salt.

Using 4-hydroxy-3-hydroxymethlpyrazole hydrochloride in place of 4(5)-hydroxymethylimidazole hydrochloride in the procedure of Example 1 gives the title compound.

EXAMPLE 34

By the procedure of Example 17, 3-(2-chloroethyl)-pyrazole (which is prepared by treating 3-(2-hydroxyethyl)-pyrazole with thionyl chloride) is reacted with cysteamine hydrochloride in the presence of aqueous potassium hydroxide to give 3-[2-(2-aminoethyl)thioethyl]pyrazole dipicrate which is converted to the dihydrochloride salt and then to the base and reacted with methyl isothiocyanate to give N-methyl-N'-[2-(2-(3-pyrazolyl)ethyl)thioethyl]thiourea.

Using ethyl isothiocyanate in place of methyl isothiocyanate, the corresponding N-ethyl compound is obtained.

Also, by the procedure of Example 1, using 3-hydroxymethylpyrazole and 3-mercaptopropylamine as the starting materials, N-methyl-N'-[3-(3-pyrazolylmethylthio)-propyl]thiourea is prepared.

EXAMPLE 35

N-Methyl-N'-[2-(3-pyrazolylmethylthio)ethyl]urea

By the procedure of Example 24, 3-[(2-aminoethyl)-thiomethyl]pyrazole is reacted with methyl isocyanate to give the title compound.

EXAMPLE 36

By the procedure of Example 18, 3-[(2-aminoethyl)-thiomethyl]pyrazole is reacted with benzoyl isothiocyanate to give N-benzoyl-N'-[2-(3-pyrazolylmethylthio)ethyl]thiourea. Removing the benzoyl group by the procedure of Example 18 gives N-[2-(3-pyrazolylmethylthio)ethyl]thiourea.

EXAMPLE 37

N-(2-Dimethylaminoethyl)-N'-[2-(3-pyrazolylmethylthio)ethyl]-thiourea

Treatment of 3-[(2-aminoethyl)thiomethyl]pyrazole with 2-dimethylaminoethyl isothiocyanate by the procedure of Example 1 gives the title compound.

EXAMPLE 38

N-Methyl-N'-[2-(3-pyrazolylmethoxy)ethyl]thiourea

3-Chloromethylpyrazole, prepared by racting 3-hydroxymethylpyrazole with thionyl chloride, is reacted with the sodium salt of ethylene glycol to give 3-(2-hydroxyethoxymethyl)-pyrazole. Treatment of 3-(2-hydroxyethoxymethyl)pyrazole with thionyl chloride gives 3-(2-chloroethoxymethyl)pyrazole.

Using 3-(2-chloroethoxymethyl)pyrazole hydrochloride (prepared from the base by treating with hydrochloric acid) in the procedure of Example 23 gives N-methyl-N'-[2-(3-pyrazolylmethoxy)ethyl]thiourea.

EXAMPLE 39

| Ingredients | Amounts |
| --- | --- |
| N-Methyl-N'-[2-(3-pyrazolylmethylthio)-ethyl]thiourea | 200 mg. |
| Lactose | 100 mg. |

The ingredients are screened, mixed and filled into a hard gelatin capsule.

Compounds of formula I wherein A is such that there is formed together with the carbon atom shown a five membered unsaturated heterocyclic ring having two nitrogen atoms and three carbon atoms, said unsaturated heterocyclic ring being imidazole or pyrazole, and Y is NH are exemplified by the following examples.

EXAMPLE 40

N-Methyl-N'-[2-(4(5)-imidazolylmethylamino)ethyl]-thiourea a. (i) 4(5)-Chloromethylimidazole (1.16 g., 0.01 m.) in 10 ml. of ethanol is added slowly to excess ethylenediamine (6.0 g.) in 25 ml. of ethanol. The mixture is heated at 55° for 1 hour, then concentrated under reduced pressure and basified with sodium hydroxide. Evaporation under high vacuo and steam distillation followed by concentration to dryness, extraction with ethanol and acidification with ethanolic hydrogen chloride gives N-(4(5)-imidazolylmethyl)-ethylenediamine. (ii) Methyl isothiocyanate (0.73 g.) is added slowly to a solution of 1.4 g. of N-(4(5)-imidazolylmethyl)ethylenediamine in 20 ml. of ethanol. The mixture is heated under reflux for 30 minutes, then concentrated and the residue separated by column chromatography to give the title compound. (b) Sodium hydride (54% suspension in mineral oil, 4.5 g.) is added to a solution of 15.6 g. of N-trifluoroacetyl-ethylenediamine in dry dimethylformamide under a nitrogen atmosphere. 4(5)-Chloromethylimidazole (11.6 g.) is added slowly and the mixture is allowed to stand overnight at room temperature. The solvent is removed under reduced pressure and the residue dissolved in a small volume of water and extracted with chloroform. The extracts are dried over anhydrous sodium sulphate, filtered and 7.3 g. of methyl isothiocyanate is added. The mixture is heated at reflux for 30 minutes, then concentrated under reduced pressure, treated with aqueous hydrogen chloride and basified with aqueous potassium carbonate to give the title compound. (c) A mixture of N-formyl-N-(4(5)-imidazolylmethyl)ethylenediamine (prepared by adding sodium hydride to N-formylethylenediamine in dry dimethylformamide, then reacting with 4(5)-chloromethylimidazole at room temperature) and methyl isothiocyanate is heated under reflux for 30 minutes, then concentrated. Treating with aqueous hydrogen chloride, then basifying with aqueous potassium carbonate gives the title compound.

EXAMPLE 41

Using, in the procedure of Example 40, in place of 4(5)-chloromethylimidazole the following compounds (which may be prepared from the corresponding hydroxymethylimidazoles by treatment with thionyl chloride):

4-chloromethyl-5-methylimidazole
4-chloromethyl-5-ethylimidazole
4-chloromethyl-5-isopropylimidazole
4-chloromethyl-5-benzylimidazole
4-chloromethyl-5-bromoimidazole
4-chloromethyl-2-methylimidazole
4-chloromethyl-1-methylimidazole
2-chloromethylimidazole
2-chloromethyl-1,5-dimethylimidazole
5-chloro-2-chloromethyl-1-methylimidazole
the products are, respectively:
 N-methyl-N'-[2-((5-methyl-4-imidazolyl)methylamino)-ethyl]thiourea
 N-methyl-N'-[2-((5-ethyl-4-imidazolyl)methylamino)ethyl]-thiourea
 N-methyl-N'-[2-((5-isopropyl-4-imidazolyl)methylamino)-ethyl]thiourea
 N-methyl-N'-[2-((5-benzyl-4-imidazolyl)methylamino)-ethyl]thiourea
 N-methyl-N'-[2-((5-bromo-4-imidazolyl)methylamino)ethyl]-thiourea
 N-methyl-N'-[2-((2-methyl-4-imidazolyl)methylamino)ethyl]-thiourea
 N-methyl-N'-[2-((1-methyl-4-imidazolyl)methylamino)ethyl]-thiourea
 N-methyl-N'-[2-(2-imidazolylmethylamino)ethyl]-thiourea
 N-methyl-N'-[2-((1,5-dimethyl-2-imidazolyl)methylamino)-ethyl]thiourea N-methyl-N'-[2-((5-chloro-1-methyl-2-imidazolyl)-
methylamino)ethyl]thiourea.

The corresponding N-ethyl compounds are prepared using ethyl isothiocyanate in place of methyl isothiocyanate.

EXAMPLE 42

Using 5-chloromethyl-4-trifluoromethylimidazole (prepared by reacting the corresponding 5-hydroxymethyl compound with thionyl chloride) in the procedure of Example 40 gives N-methyl-N'-[2-((4-trifluoromethyl-5-imidazolyl)methylamino)ethyl]thiourea.

Also, using 2-amino-4-chloromethylimidazole in the procedure of Example 40 gives N-methyl-N'-[2-((2-amino-4-imidazolyl)methylamino)ethyl]thiourea.

Reacting N-(4(5)-imidazolylmethyl)ethylenediamine with methyl isocyanate by the procedure of Example 24, then concentrating and separating the residue by column chromatography gives N-methyl-N'-[2-(4(5)-imidazolylmethylamino)ethyl]urea.

Using 4(5)-chloromethylimidazole and 1,3-diaminopropane as starting materials in the procedure of Example 40 gives N-methyl-N'-[3-(4(5)-imidazolylmethylamino)propyl]-thiourea.

EXAMPLE 43

N-Methyl-N'-[2-(2-(4(5)-imidazolyl)ethylamino)ethyl]thiourea

By the procedure of Example 40 using 4(5)-(2-chloroethyl)imidazole, the product is N-methyl-N'-[2-(2-(4(5)-imidazolyl)ethylamino)ethyl]thiourea.

EXAMPLE 44

4,5-bis-[2-(N-Methylthioureido)ethylaminomethyl]imidazole

Using 4,5-di(chloromethyl)imidazole in the procedure of Example 40 gives the title compound.

EXAMPLE 45

N-Methyl-N'-[2-((5-methyl-4-imidazolyl)methylamino)ethyl]urea

By the procedure of Example 24, N-(5-methyl-4-imidazolylmethyl)ethylenediamine is reacted with methyl isocyanate to give, after concentrating and separating the residue by column chromatography, the title compound.

EXAMPLE 46

N-[2-(4(5)-Imidazolylmethylamino)ethyl]thiourea

A mixture of 6.0 g. of N-(4(5)-imidazolylmethyl)-ethylenediamine and 6.0 g. of benzoyl isothiocyanate in 150 ml. of chloroform is heated under reflux for one hour, then concentrated and chromatographed to give N-benzoyl-N'-[2-(4(5)-imidazolylmethylamino)ethyl]-thiourea.

The benzoyl thiourea is added to a solution of potassium carbonate in water at 60° C. The mixture is maintained at this temperature for one hour, then concentrated and acidified with hydrochloric acid. The mixture is filtered and the filtrate is basified with potassium carbonate, concentrated and extracted with isopropyl alcohol. The extract is concentrated to give N-[2-(4(5)-imidazolylmethylamino)ethyl]thiourea.

EXAMPLE 47

N-(2-Dimethylaminoethyl)-N'-[2-(4(5)-imidazolylmethylamino)-ethyl]thiourea

Treating N-(4(5)-imidazolylmethyl)ethylenediamine with 2-dimethylaminoethyl isothiocyanate, then concentrating and separating by column chromatography by the procedure of Example 40(a)(ii) gives N-(2-dimethylaminoethyl)-N'-[2-(4(5)-imidazolylmethyl)amino)ethyl]thiourea.

EXAMPLE 48

Treating the product of Example 40 with hydrochloric acid gives N-methyl-N'-[2-(4(5)-imidazolylmethylamino)ethyl]-thiourea hydrochloride.

Treating N-methyl-N'-[2((5-methyl-4-imidazolyl)-methylamino)ethyl]thiourea with maleic acid in ethanol gives the maleate salt.

EXAMPLE 49

| Ingredients | Amounts |
|---|---|
| N-Methyl-N'-[2-(4(5)-imidazolylmethylamino)-ethyl]thiourea | 200 mg. |
| Sucrose | 75 mg. |
| Starch | 25 mg. |
| Talc | 5 mg. |
| Stearic acid | 2 mg. |

The ingredients are screened, mixed and filled into a hard gelatin capsule.

EXAMPLE 50

| Ingredients | Amounts |
|---|---|
| N-Methyl-N'-[2-((5-methyl-4-imidazolyl)methyl)-amino)ethyl]thiourea | 150 mg. |
| Lactose | 100 mg. |

The ingredients are screened, mixed and filled into a hard gelatin capsule.

EXAMPLE 51

Using, in the procedure of Example 40, the following bromomethylpyrazoles (which may be prepared by treating the hydroxymethylpyrazoles with thionyl bromide):

3-bromomethylpyrazole
5-methyl-3-bromomethylpyrazole
3,5-dimethyl-4-bromomethylpyrazole
5-hydroxy-3-bromomethylpyrazole
3,4-di(bromomethyl)pyrazole the products are, respectively:

N-methyl-N'-[2-(3-pyrazolylmethylamino)ethyl]thiourea
N-methyl-N'-[2-((5-methyl-3-pyrazolyl)methylamino)-ethyl]thiourea
N-methyl-N'-[2-((3,5-dimethyl-4-pyrazolyl)methylamino)-ethyl]thiourea
N-methyl-N'-[2-((5-hydroxy-3-pyrazolyl)methylamino)-ethyl]thiourea
3,4-bis-[2-(N-methylthioureido)ethylaminomethyl]-pyrazole.

Similarly, using 3-(2-bromoethyl)pyrazole in the procedure of Example 40, the product is N-methyl-N'-[2-(2-(3-pyrazolyl)ethylamino)ethyl]thiourea.

Also, in the procedure of Example 40, using 3-bromomethylpyrazole and 1,3-diaminopropane, the product is N-methyl-N'-[3-(3-pyrazolylmethylamino)-propyl]thiourea.

Using ethyl isothiocyanate in place of methyl isothiocyanate the corresponding N-ethyl compounds are prepared.

EXAMPLE 52

N-Methyl-N'-[2-((4-hydroxy-3-pyrazolyl)methylamino)ethyl]-thiourea

4-Hydroxy-3-hydroxymethylpyrazole (which is prepared by converting 4-hydroxy-3-pyrazolecarboxylic acid to its ethyl ester and reducing the ester with lithium aluminium hydride) is treated with thionyl bromide at room temperature to give 3-bromomethyl-4-hydroxypyrazole.

Using 3-bromomethyl-4-hydroxypyrazole in the procedure of Example 40 gives the title compound.

EXAMPLE 53

The reaction of 8.3 g. (0.1 m.) of 3-aminopyrazole and 13.3 g. (0.1 m.) of β-azidopropionyl chloride in pyridine gives 3-(β-azidopropionamido)pyrazole. Reduction of this compound with diborane in ethylene glycol/dimethyl ether yields 3-(3-aminopropylamino)-pyrazole.

A mixture of 2.55 g. of 3-(3-aminopropylamino)-pyrazole and 1.46 g. of methyl isothiocyanate in 50 ml. of isopropyl alcohol is stirred at room temperature for 16 hours to give, after concentrating and triturating the residue under methyl ethyl ketone, N-methyl-N'-[3-(3-pyrazolylamino)propyl]thiourea.

By the same procedure, starting from 2-aminoimidazole, N-methyl-N'-[3(2-imidazolylamino)-propyl]thiourea is prepared.

EXAMPLE 54

By the procedure of Example 46, reacting 3-(3-aminopropylamino)pyrazole (prepared as in Example 53) with benzoyl isothiocyanate gives N-benzoyl-N'-[3-(3-pyrazolylamino)propyl]thiourea.

Treating the benzoyl thiourea with potassium carbonate by the procedure of Example 46 gives N-[3-(3-pyrazolylamino)propyl]thiourea.

EXAMPLES 55

N-(2-Dimethylaminoethyl)-N'-[2-(3-pyrazolylmethylamino)ethyl]-thiourea

Treating N-(3-pyrazolylmethyl)ethylenediamine with 2-dimethylaminoethyl isothiocyanate by the procedure of Example 40 gives the title compound.

EXAMPLE 56

N-MethylN'-[2-(3-pyrazolylmethylamino)ethyl]urea

N-(3-Pyrazolylmethyl)ethylenediamine is reacted with methyl isocyanate by the procedure of Example 24 to give, after concentrating and separating the residue by column chromatography, the title compound.

EXAMPLE 57

Treating N-[3-(3-pyrazolylamino)propyl]thiourea with maleic acid in ethanol gives the maleate salt.

Treating N-methyl-N'-[2-(3-pyrazolylmethylamino)-ethyl]thiourea with hydrobromic acid gives the hydrobromide salt.

EXAMPLE 58

| Ingredients | Amounts |
| --- | --- |
| N-Methyl-N'-[2-(3-pyrazolylmethylamino)-ethyl]thiourea | 200 mg. |
| Lactose | 100 mg. |

The ingredients are screened, mixed and filled into a hard gelatin capsule.

Compounds of formula I wherein A is such that there is formed together with the carbon atom shown a six membered unsaturated heterocyclic ring having two nitrogen atoms and four carbon atoms, said unsaturated heterocyclic ring being pyrimidine, pyrazine or pyridazine, and Y is oxygen or sulphur (sulphur is preferred) are exemplified by the following examples.

EXAMPLES 59

N-Methyl-N'-[2-(2-pyrimidylmethylthioethyl]thiourea

A mixture of 5-bromo-2-hydroxymethylpyrimidine (5.6 g.) and magnesium oxide (5.6 g.) in water/ethanol (2:1) was submitted to hydrogenolysis over 10% palladised charcoal for 0.5 hours. Filtration, concentration and ether extraction from an aqueous solution of the residue afforded 2-hydroxymethylpyrimidine (1.85 g.) as a mobile liquid.

The reaction of 2-chloromethylpyrimidine (prepared from the hydroxymethyl compound by reaction thereof with thionyl chloride) with phthalimidoethanethiol, hydrazinolysis to remove the protecting phthalimido group and reaction of the product with methyl isothiocyanate, according to the method described in Example 1, gave N-methyl-N'-[2-(2-pyrimidylmethylthio)ethyl]thiourea.

EXAMPLE 60

Using the following chloromethylpyrimidine compounds (prepared where necessary from the corresponding hydroxymethyl compounds and thionyl chloride) in the procedure of Example 50:

4-chloromethyl-6-methylpyrimidine
2-chloromethyl-5-methylpyrimidine
4-hydroxy-2-chloromethylpyrimidine
5-bromo-2-chloromethylpyrimidine
2-chloro-4-chloromethylpyrimidine
2-amino-4-chloromethylpyrimidine
5-chloromethyl-2,4-dimethylpyrimidine
4-chloro-2-methyl-5-chloromethylpyrimidine the products are, respectively:
N-methyl-N'-[2-((6-methyl-4-pyrimidyl)methylthio)ethyl]-thiourea
N-methyl-N'-[2-((5-methyl-2-pyrimidyl)methylthio)ethyl]-thiourea
N-methyl-N'-[2-((4-hydroxy-2-pyrimidyl)methylthio)ethyl]thiourea
N-methyl-N'-[2-((5-bromo-2-pyrimidyl)methylthio)ethyl]-thiourea
N-methyl-N'-[2-((2-chloro-4-pyrimidyl)methylthio)ethyl]thiourea N-methyl-N'-[2-((2-amino4-pyrimidyl)methylthio)ethyl]thiourea N-methyl-N'-[2-((2,4-dimethyl-5-pyrimidyl)methylthio)-ethyl]thiourea N-methyl-N'-[2-((4-chloro-2-methyl-5-pyrimidyl)methlthio)-ethyl]thiourea.

The corresponding N-ethyl compounds are prepared using ethyl isothiocyanate in place of methyl isothiocyanate.

In the procedure of Example 1(i)(b) and (ii), using 2-chloromethylpyrimidine and 3-phthalimidopropanethiol as the starting materials, the product is N-methyl-N'-[3-(2-pyrimidylmethylthio)propyl]thiourea.

EXAMPLE 61

4,6-bis-[2-N-Methylthioureido)ethylthiomethyl]-pyrimidine

4,6-Pyrimidinedicarboxylic acid is converted to the diethyl ester which is reduced with lithium aluminium hydride in tetrahydrofuran to give 4,6-di(hydroxymethyl)-pyrimidine which on treatment with thionyl chloride gives 4,6-di(chloromethyl)pyrimidine.

Using 4,6-di(chloromethyl)pyrimidine in the procedure of Example 59 give the title compound.

EXAMPLE 62

N-Methyl-N'-[2(2-pyrimidylmethylthio)ethyl]urea

By the procedure of Example 24, 2-[(2-aminoethyl)-thiomethyl]pyrimidine is reacted with methyl isocyanate to give the title compound.

EXAMPLE 63

N-Methyl-N'-[2-(2-(4-pyrimidyl)ethyl)thioethyl]thiourea

By the procedure of Example 17, using 4-(2-chloroethyl)pyrimidine, prepared by treating 4-(2-hydroxyethyl)pyrimidine with thionyl chloride, as the starting material, the title compound is prepared.

EXAMPLE 64 i. A mixture of 2-mercaptopyrimidine (5.6 g.) and 3-bromopropylphthalimide (13.4 g.) in ethanol (100 ml.) containing sodium (1.15 g.) was heated under reflux for 20 hours affording 2-(3-phthalimidopropylthio)pyrimidine, m.p. 81.5°–82.5° (from ethanol-water).

ii. Reaction of the phthalimido compound (3.7 g.) with hydrazine (1.86 g.) followed by reaction of the product directly with methyl isothiocyanate (0.83 g.), afforded N-methyl-N'-[3-(2-pyrimidylthio)propyl]thiourea (1.9 g.), m.p. 120°–121° (from ethanol-ether).

By the same procedure, using 4-me capto-2-trifluoromethylpyrimidine (prepared by reacting 4-hydroxy-2-trifluoromethylpyrimidine with phosphorus pentasulfide), N-methyl-N'-[3-((2-trifluoromethyl-4-pyrimidyl)thio)propyl[-thiourea is obtained.

EXAMPLE 65

N-Methy-N'-[2-(2-pyrimidylmethoxy)ethyl]thiourea

By the procedure of Example 38, 2-chloromethylpyrimidine prepared by reacting 2-hydroxymethylpyrimidine with thionyl chloride, is converted to 2-(2-chloroethoxymethyl)pyrimidine hydrochloride.

Using 2-(2-chloroethoxymethyl)pyrimidine in the procedure of Example 23 gives the title compound.

EXAMPLE 66

By the procedure of Example 18, 2-[(2-aminoethyl)-thiomethyl]pyrimidine is reacted with benzoyl isothiocyanate to give N-benzoyl-N'-[2-(2-pyrimidylmethylthio)ethyl]thiourea. Removing the benzoyl group by the procedure of Example 18 give N-[2-(2-pyrimidylmethlthio)ethyl]thiourea.

EXAMPLE 67

N-(2-Dimethylaminoethyl)-N'-[2-(2-pyrimidylmethylthio)ethyl]-thiourea

Treatment of 2-[(2-aminoethyl)thiomethyl]pyrimidine with 2-dimethylaminoethyl isothiocyanate by the procedure of Example 1 gives the title compound.

EXAMPLE 68

| Ingredients | Amounts |
| --- | --- |
| N-Methyl-N'-[2-(2-pyrimidylmethylthio)-ethyl]thiourea | 150 mg. |
| Sucrose | 70 mg. |
| Starch | 25 mg. |
| Talc | 5 mg. |
| Stearic acid | 2 mg. |

The ingredients are screened, mixed and filled into a hard gelatin capsule.

EXAMPLE 69

| Ingredients | Amounts |
| --- | --- |
| N-Methyl-N'-[2-(2-pyrimidylmethylthio)-ethyl]thiourea | 200 mg. |
| Lactose | 100 mg. |

The ingredients are screened, mixed and filled into a hard gelatin capsule.

EXAMPLE 70

N-Methyl-N'-[2-(2-pyrazinylmethylthio)ethyl]thiourea i. 2-Chloromethylpyrazine (6.4 g.) was added over 20 minutes to a solution freshly prepared from sodium (0.23 g.) in ethanol (50 ml.) to which cysteamine hydrochloride (5.7 g.) had been added gradually at 0° and stirred at this temperature for 2 hours. The suspension finally obtained was stirred at room temperature overnight, acidified with hydrochloric acid (pH 5) and concentrated under reduced pressure. The dry residue was extracted with ethanol and the extracts filtered and concentrated to give the crude product. Extraction with isopropyl alcohol, with the removal of some polymeric material and the addition of ether gave a cream colored solid (3.5 g.), which was recrystallised from ethanol-ether to furnish 2-[(2-aminoethyl)thiomethyl]-pyrazine hydrochloride, m.p. 144°–146°.

ii. The amine hydrochloride (1.6 g.) was converted into the free base using potassium carbonate and reacted with methyl isothiocyanate (0.61 g.) in ethanol in the usual way. Recrystallisation from ethanol furnished N-methyl-N'-[2-(2-pyrazinylmethylthio)ethyl]thiourea (0.88 g.), m.p. 99.5°–100.5°. (Found: C, 44.6; H, 5.9; N, 22.8; S, 26.5; $C_9H_{14}N_4S$ requires: C, 44.6; H, 5.8; N, 23.1; S, 26.5).

EXAMPLE 71

Using, in the procedure of Example 70, the following haloalkylpyrazines, which may be prepared by reacting the hydroxyalkylpyrazines with a thionyl halide:

2-chloromethyl-5-methylpyrazine
2-chloromethyl-3-methylpyrazine
3-chloro-2-chloromethylpyrazine
3-amino-2-chloromethylpyrazine
2,3-di(chloromethyl)pyrazine the products are, respectively:

N-methyl-N'-[2-((5-methyl-2-pyrazinyl)methylthio)ethyl]-thiourea
N-methyl-N'-[2-((3-methyl-2-pyrazinyl)methylthio)ethyl]-thiourea
N-methyl-N'-[2-((3-chloro-2-pyrazinyl)methylthio)ethyl]-thiourea
N-methyl-N'-[2-((3-amino-2-pyrazinyl)methylthio)ethyl]-thiourea
2,3-bis- 2-(N-methylthioureido)ethylthiomethyl pyrazine.

Also, by the procedure of Example 70, reacting 2-[(2-aminoethyl)thiomethyl]pyrazine with ethyl isothiocyanate gives N-ethyl-N-[2-(2-pyrazinylmethylthio)ethyl]thiourea.

In the procedure of Example 70, using 3-mercaptopropylamine in place of cysteamline, the product is N-methyl-N'-[3-(2-pyrazinylmethylthio)propyl]thiourea.

EXAMPLE 72

3-Hydroxypyrazine-2-carboxylic acid is converted to the corresponding ethyl ester and the ester is reduced with lithium aluminium hydride in tetrahydrofuran to give 3-hydroxy-2-hydroxymethylpyrazine.

Treatment of 3-hydroxy-2-hydroxymethylpyrazine at room temperature with thionyl chloride gives 2-chloromethyl-3-hydroxypyrazine.

Using 2-chloromethyl-3-hydroxypyrazine in the procedure of Example 70, the product is N-methyl-N'-[2-((3-hydroxy-2-pyrazinyl)methylthio)ethyl]thiourea.

By the same procedure, using 3,6-dimethylpyrazine-2-carboxylic acid as the starting material, the product is N-methyl-N'-[2-((3,6-dimethyl-2-pyrazinyl)methylthio)ethyl]-thiourea.

Reduction of 3-chloro-5-methyl-2-pyrazinecarboxylic acid (prepared by alkaline hydrolysis of the methyl ester) with diborane gives 3-chloro-2-hydroxymethyl-5-methylpyrazine which, using the above procedure, yields N-methyl-N'-[2-((3-chloro-5-methyl-2-pyrazinyl)methylthio)ethyl]thiourea.

EXAMPLE 73

N-Methyl-N'-[2-(2-(2-pyrazinyl)ethyl)thioethyl]thiourea

Using, in the procedure of Example 17, 2-(2-chloroethyl)pyrazine, prepared by reacting 2-(2-hydroxyethyl)-pyrazine with thionyl chloride, as the starting material gives the title compound.

EXAMPLE 74

N-Methyl-N'-[3-(2-pyrazinylthio)propyl]thiourea

Using, in the procedure of Example 64, 2-mercaptopyrazine as the starting material, the title compound is obtained.

EXAMPLE 75

N-Methyl-N'-[2-(2-pyrazinylmethoxy)ethyl]thiourea

Using, in the procedure of Example 38, 2-chloromethylpyrazine as the starting material, the product is the title compound.

EXAMPLE 76

N-Methyl-N'-[2-((2-pyrazinyl)methlthio)ethyl]urea

By the procedure of Example 24, 2-[(2-aminoethyl)thiomethyl]pyrazine is reacted with methyl isocyanate to give the title compound.

EXAMPLE 77

By the procedure of Example 18, 2-[(2-aminoethyl)thiomethyl]pyrazine is reacted with benzoyl isothiocyanate to give N-benzoyl-N'-[2-(2-pyrazinylmethylthio)ethyl]thiourea. Removing the benzoyl group by the procedure of Example 18 gives N-[2-(2-pyrazinylmethylthio)ethyl]thiourea.

EXAMPLE 78

N-(2-Dimethylaminoethyl)-N'-[2-(2-pyrazinylmethylthio)ethyl]-thiourea

Treatment of 2-[(2-aminoethyl)thiomethyl]pyrazine with 2-dimethylaminomethyl isothiocyanate by the procedure of Example 1 gives the title compound.

EXAMPLE 79

| Ingredients | Amounts |
| --- | --- |
| N-Methyl-N'-[2-(2-pyrazinylmethylthio)-ethyl]thiourea | 200 mg. |
| Lactose | 100 mg. |

The ingredients are mixed and filled into a hard gelatin capsule.

EXAMPLE 80

N-Methyl-N'-[2-(3-pyridazinylmethylthio)ethyl]thiourea

By the procedure of Example 1, using 3-hydroxymethylpyridazine, the intermediate 3-[(2-aminoethyl)thiomethyl]pyridazine dipicrate, m.p. 145°–148°, and the product, N-methyl-N'-[2-(3-pyridazinylmethylthio)ethyl]thiourea (recrystallised from acetone-ether), m.p. 110°–111°, were obtained. (Found: C, 44.5; H, 5.9, N, 23.0; S, 26.3. $C_9H_{14}N_4S_2$ requires: C, 44.6; H, 5.8; N, 23.1; S, 26.5).

EXAMPLE 81

Using in the procedure of Example 1 the following hydroxymethylpyridazines:

4-hydroxymethyl-6-methylpyridazine
4-hydroxymethyl-3,6-dimethylpyridazine
3-chloro-4-hydroxymethyl-6-methylpyridazine
4,5-di(hydroxymethyl)pyridazine the products are, respectively:
N-methyl-N'-[2-((6-methyl-4-pyridazinyl)methylthio)-ethyl]thiourea
N-methyl-N'-[2-((3,6-dimethyl-4-pyridazinyl)methylthio)-ethyl]thiourea N-methyl-N'-[2-((3-chloro-6-methyl-4-pyridazinyl)methylthio)ethyl]thiourea 4,5-bis-[2-(N-methylthioureido)ethylthiomethyl]pyridazine.

Using ethyl isothiocyanate in place of methyl isothiocyanate in the procedure of Example 1, the corresponding N-ethyl compounds are prepared.

In the procedure of Example 1, using 4-hydroxymethyl-6-methylpyridazine and 3-mercaptopropylamine as the starting materials, the product is N-methyl-N'-[3-((6-methyl-4-pyridazinyl)methylthio)propyl]thiourea.

EXAMPLE 82

6-Amino-3-pyridazinecarboxylic acid is converted to the methyl ester and the ester is reduced with lithium aluminium hydride in tetrahydrofuran to give 6-amino-3-hydroxymethylpyridazine.

Using 6-amino-3-hydroxymethylpyridazine in the procedure of Example 1 gives N-methyl-N'-[2-((6-amino-3-pyridazinyl)methylthio)ethyl]thiourea.

By the same procedure, using 6-hydroxy-3-pyridazinecarboxylic acid as the starting material, the product is N-methyl-N'-[2-((6-hydroxy-3-pyridazinyl)methyl-thio)ethyl]thiourea.

Reduction of 6-chloro-3-pyridazinecarboxylic acid with diborane gives 6-chloro-3-hydroxymethylpyridazine which, in the procedure of Example 1, yields N-methyl-N'-[2-((6-chloro-3-pyridazinyl)methylthio)ethyl]thiourea.

EXAMPLE 83

N-Methyl-N'-[2-(3-pyridazinylmethylthio)ethyl]urea

By the procedure of Example 24, 3-[(2-aminoethyl)thiomethyl]pyridazine is reacted with methyl isocyanate to give the title compound.

EXAMPLE 84

By the procedure of Example 18, 3-[(2-aminoethyl)thiomethyl]pyridazine is reacted with benzoyl isothiocyanate to give N-benzoyl-N'-[2-(3-pyridazinylmethylthio)ethyl]thiourea. Removing the benzoyl group by the procedure of Example 18 gives N-[2-(3-pyridazinylmethylthio)ethyl]thiourea.

EXAMPLE 85

N-(2-Dimethylaminoethyl)-N'-[2-(3-pyridazinylmethylthio)-ethyl]thiourea

Treatment of 3-[(2-aminoethyl)thiomethyl]-pyridazine with 2-dimethylaminoethyl isothiocyanate by the procedure of Example 1 gives the title compound.

EXAMPLE 86

N-Methyl-N'-[2-(3-pyridazinylmethoxy)ethyl]thiourea

By the procedure of Example 38, using 3-chloromethylpyridazine (prepared by treating 3-hydroxymethylpyridazine with thionyl chloride) as the starting material, the product is the title compound.

EXAMPLE 87

3-Cyanomethylpyridazine is treated with aqueous sodium hydroxide to give 3-pyridazineacetic acid.

3-Pyridazineacetic acid is esterified with anhydrous ethanolic hydrogen chloride and the resulting ethyl ester is reduced with lithium aluminum hydride in tetrahydrofuran to give 3-(2-hydroxyethyl)pyridazine.

Treating this hydroxyethyl compound with thionyl chloride gives 3-(2-chloroethyl)pyridazine.

Using 3-(2-chloroethyl)pyridazine as the starting material in the procedure of Example 17 gives N-methyl-N'-[2-(2-(3-pyridazinyl)ethyl)thioethyl]thiourea.

EXAMPLE 88

N-Methyl-N'-[3-(3-pyridazinylthio)propyl]thiourea

Using 3-mercaptopyridazine as the starting material in the procedure of Example 21, the title compound is obtained.

EXAMPLE 89

| Ingredients | Amounts |
|---|---|
| N-Methyl-N'-[2-(3-pyridazinylmethylthio)-ethyl]thiourea | 150 mg. |
| Lactose | 150 mg. |

The ingredients are mixed and filled into a hard gelatin capsule.

Compounds of formula I wherein A is such that there is formed together with the carbon atom shown a six membered unsaturated heterocyclic ring having two nitrogen atoms and four carbon atoms, said unsaturated heterocyclic ring being pyrimidine, pyrazine or pyridazine, and Y is NH are exemplified by the following examples.

EXAMPLE 90

Using, in the procedure of Example 40 (a), the following haloalkylpyrimidines (which may be prepared by treating the hydroxyalkylpyrimidines with a thionyl halide):

2-chloromethylpyrimidine
5-bromomethylpyrimidine
2-chloromethyl-5-methylpyrimidine
5-bromo-2-bromomethylpyrimidine
2-bromomethyl-4-hydroxypyrimidine
4-amino-5-bromomethylpyrimidine
5-bromomethyl-2,4-dimethylpyrimidine
4-chloro-5-chloromethyl-2-methylpyrimidine
4,6-di(bromomethyl)pyrimidine
the products are, respectively:
  N-methyl-N'-[2-(2-pyrimidylmethylamino)ethyl]thiourea
  N-methyl-N'-[2-(5-pyrimidylmethylamino)ethyl]thiourea
  N-methyl-N'-[2-((5-methyl-2-pyrimidyl)methylamino)-ethyl]thiourea
  N-methyl-N'-[2-((5-bromo-2-pyrimidyl)methylamino)-ethyl]thiourea
  N-methyl-N'-[2-((4-hydroxy-2-pyrimidyl)methylamino)-ethyl]thiourea
  N-methyl-N'-[2-((4-amino-5-pyrimidyl)methylamino)-ethyl]thiourea
  N-methyl-N'-[2-((2,4-dimethyl-5-pyrimidyl)methylamino)-ethyl]thiourea
  N-methyl-N'-[2-((4-chloro-2-methyl-5-pyrimidyl)methyl-amino)ethyl]thiourea
  4,6-bis-[2-(N-methylthioureido)ethylaminomethyl]pyrimidine.

Also, using in the procedure of Example 40 (a), 2-chloromethylpyrimidine and 1,3-diaminopropane, the product is N-methyl-N'-[3-(2-pyrimidylmethylamino)-propyl]-thiourea.

EXAMPLE 91

N-Methyl-N'-[2-(2-pyrimidylmethylamino)ethyl]urea

By the procedure of Example 24, N-(2-pyrimidylmethyl)ethylenediamine is reacted with methyl isocyanate to give, after concentrating and separating the residue by column chromatography, the title compound.

EXAMPLE 92

N-Methyl-N'-[2-(2-(4-pyrimidyl)ethyl)aminoethyl]-thiourea

Usng, in the procedure of Example 40 (a), 4-(2-chloroethyl)pyrimidine (prepared by reacting 4-(2-hydroxyethyl)pyrimidine with thionyl chloride) as the starting material, the title compound is prepared.

EXAMPLE 93

Reaction of 2-bromopyrimidine with 1,3-diaminopropane in ethanol containing sodium ethoxide gives 2-(3-aminopropylamino)pyrimidine which on reaction with methyl isothiocyanate results in the production of N-methyl-N'-[3-(2-pyrimidylamino)propyl]thiourea.

Similarly, using 4-chloro-2-trifluoromethylpyrimidine (prepared by treating 4-hydroxy-2-trifluoromethylpyrimidine with phosphorus oxychloride and dimethylaniline), the product is N-methyl-N'-[3-((2-trifluoromethyl-4-pyrimidyl)amino)propyl]thiourea.

EXAMPLE 94

By the procedure of Example 46, N-(2-pyrimidylmethyl)ethylenediamine is reacted with benzoyl isothiocyanate to give N-benzoyl-N'-[2-(2-pyrimidylmethylamino)-ethyl]thiourea.

Removing the benzoyl group by the procedure or Example 46 gives N-[2-(2-pyrimidylmethylamino)ethyl]thiourea. Treatment with hydrobromic acid gives the hydrobromide salt.

EXAMPLE 95

Reacting 2-(3-aminopropylamino)pyrimidine, prepared by reacting 2-bromopyrimidine with 1,3-diaminopropane, with benzoyl isothiocyanate by the procedure of Example 46 gives N-benzoyl-N'-[3-(2-pyrimidylamino)propyl]thiourea.

Removing the benzoyl group by the procedure of Example 46 gives N-[3-(2-pyrimidylamino)propyl]thiourea.

EXAMPLE 96

N-(2-Dimethylaminoethyl)-N'-[2-(2-pyrimidylmethylamino)-ethyl]thiourea

Treating N-(2-pyrimidylmethyl)ethylenediamine with 2-dimethylaminoethyl isothiocyanate, then concentrating and separating by column chromatography by the procedure of Example 40 (a)(ii) gives the title compound.

EXAMPLE 97

| Ingredients | Amounts |
| --- | --- |
| N-Methyl-N'-[2-(2-pyrimidylmethylamino)-ethyl]thiourea | 200 mg. |
| Lactose | 100 mg. |

The ingredients are mixed and filled into a hard gelatin capsule.

EXAMPLE 98

Using, in the procedure of Example 40 (a), the following haloalkylpyrazines:

2-chloromethylpyrazine
2-chloromethyl-5-methylpyrazine
2-chloromethyl-3-methylpyrazine
3-chloro-2-chloromethylpyrazine
3-amino-2-chloromethylpyrazine
2,3-di(chloromethyl)pyrazine
2-chloromethyl-3-hydroxypyrazine
2-chloromethyl-3,6-dimethylpyrazine
3-chloro-2-chloromethyl-5-methylpyrazine
2-(2-chloroethyl)pyrazine the products are, respectively:
N-methyl-N'-[2-(2-pyrazinylmethylamino)ethyl]thiourea
N-methyl-N'-[2-((5-methyl-2-pyrazinyl)methylamino)ethyl]thiourea
N-methyl-N'-[2-((3-methyl-2-pyrazinyl)methylamino)-ethyl]thiourea
N-methyl-N'-[2-((3-chloro-2-pyrazinyl)methylamino)-ethyl]thiourea
N-methyl-N'-[2-((3-amino-2-pyrazinyl)methylamino)-ethyl]thiourea
2,3-bis-[2-(N-methylthioureido)ethylaminomethyl]-pyrazine
N-methyl-N'-[2-((3-hydroxy-2-pyrazinyl)methylamino)-ethyl]thiourea
N-methyl-N'-[2-((3,6-dimethyl-2-pyrazinyl)methylamino)-ethyl]thiourea
N-methyl-N'-[2-((3-chloro-5-methyl-2-pyrazinyl)methyl-amino)ethyl]thiourea
N-methyl-N'-[2-(2-(2-pyrazinyl)ethyl)aminoethyl]-thiourea Treatment of N-methyl-N'-[2-(2-(2-pyrazinyl)ethyl)-aminoethyl]thiourea with hydriodic acid gives the hydroiodate salt.

Also, in the procedure of Example 40, using 2-chloromethylpyrazine and 1,3-diaminopropane, the product is N-methyl-N'-[3-(2-pyrazinylmethylamino)-propyl]thiourea.

EXAMPLE 99

N-Methyl-N'-[2-(2-pyrazinylmethylamino)ethyl]urea

Reacting N-(2-pyrazinylmethyl)ethylenediamine with methyl isocyanate by the procedure of Example 24, then concentrating and separating the residue by column chromatography gives the title compound.

EXAMPLE 100

N-Methyl-N'-[3-(2-pyrazinylamino)propyl]thiourea

Reacting 2-chloropyrazine with 1,3-diaminopropane by the procedure of Example 93 gives 2-(3-aminopropylamino)-pyrazine and reacting this intermediate with methyl isothiocyanate gives the title compound.

EXAMPLE 101

Reacting 2-(3-aminopropylamino)pyrazine with benzoyl isothiocyanate by the procedure of Example 46 gives N-benzoyl-N'-[3-(2-pyrazinylamino)propyl]thiourea. Removing the benzoyl group by the procedure of Example 46 gives N-[3-(2-pyrazinylamino)propyl]thiourea.

Treating this compound with hydrochloric acid gives the hydrochloride salt.

Reacting 2-(3-aminopropylamino)pyrazine with ethyl isothiocyanate by the procedure of Example 53 gives N-ethyl-N'-[3-(2-pyrazinylamino)propyl]thiourea.

EXAMPLE 102

N-(2-Dimethylaminoethyl)-N'-[2-(2-pyrazinylmethylamino)-ethyl]thiourea

By the procedure of Example 40 (a), treating N-(2-pyrazinylmethyl)ethylenediamine with 2-dimethylaminoethyl isothiocyanate gives the title compound.

EXAMPLE 103

| Ingredients | Amounts |
| --- | --- |
| N-Methyl-N'-[2-(2-pyrazinylmethylamino)-ethyl]thiourea | 200 mg. |
| Lactose | 150 mg. |

The ingredients are mixed and filled into a hard gelatin capsule.

EXAMPLE 104

Using, in the procedure of Example 40, the following chloroalkylpyridazines (which may be prepared by treating the hydroxyalkylpyridazines with thionyl chloride):

3-chloromethylpyridazine
4-chloromethyl-6-methylpyridazine
4-chloromethyl-3,6-dimethylpyridazine
3-chloro-4-chloromethyl-6-methylpyridazine
4,6-di(chloromethyl)pyridazine
6-amino-3-chloromethylpyridazine
6-chloro-3-chloromethylpyridazine
3-chloromethyl-6-hydroxypyridazine
the products are, respectively:
  N-methyl-N'-[2-(3-pyridazinylmethylamino)ethyl]-thiourea
  N-methyl-N'-[2-((6-methyl-4-pyridazinyl)methylamino)ethyl]-thiourea
  N-methyl-N'-[2-((3,6-dimethyl-4-pyridazinyl)methylamino)-ethyl]thiourea
  N-methyl-N'-[2-((3-chloro-6-methyl-4-pyridazinyl)-methyl-amino)ethyl]thiourea
  4,6-bis-[2-(N-methylthioureido)ethylaminomethyl]-pyridazine
  N-methyl-N'-[2-((6-amino-3-pyridazinyl)methylamino)ethyl]-thiourea
  N-methyl-N'-[2-((6-chloro-3-pyridazinyl)methylamino)ethyl]-thiourea
  N-methyl-N'-[2-((6-hydroxy-3-pyridazinyl)methylamino)-ethyl]thiourea.

Treatment of N-methyl-N'-2-(3-pyridazinylmethylamino)ethyl]thiourea with hydrobromic acid gives the hydrobromide salt.

Also, by the procedure of Example 40, using 3-chloromethylpyridazine and 1,3-diaminopropane, the product is N-methyl-N'-[3-(3-pyridazinylmethylamino)propyl]-thiourea.

EXAMPLE 105

N-Methyl-N'-[2-(3-pyridazinylmethylamino)ethyl-]urea

Reacting N-(3-pyridazinylmethyl)ethylenediamine with methyl isocyanate by the procedure of Example 24, then concentrating and separating the residue by column chromatography gives the title compound.

EXAMPLE 106

N-(2-Dimethylaminoethyl)-N'-[2-(3-pyridazinylmethylamino)-ethyl]thiourea

Reacting N-(3-pyridazinylmethyl)ethylenediamine with 2-dimethylaminoiethyl isothiocyanate by the procedure of Example 40 gives the title compound.

EXAMPLE 107

N-Methyl-N'-[3-(3-pyridazinylamino)propyl]thiourea

Using, in he procedure of Example 93, 3-chloropyridazine as the starting material, the title compound is prepared.

EXAMPLE 108

Treating 3-(3-aminopropylamino)pyridazine, prepared by reacting 3-chloropyridazine with 1,3-diaminopropane, with benzoyl isothiocyanate by the procedure of Example 46 gives N-benzoyl-N'-[3-(3-pyridazinylamino)propyl]-thiourea. Removing the benzoyl group by the procedure of Example 46 gives N-[3-(3-pyridazinylamino)propyl]thiourea.

Reacting 3-(3-aminopropylamino)pyridazine with ethyl isothiocyanata by the procedure of Example 53 gives N-ethyl-N-[3-(3-pyridazinylamino)propyl]thiourea.

EXAMPLE 109

| Ingredients | Amounts |
| --- | --- |
| N-Methyl-N'-[2-(3-pyridazinylmethylamino)-ethyl]thiourea | 200 mg. |
| Lactose | 100 mg. |

The ingredients are mixed and filled into a hard gelatin capsule.

Compounds of formula I wherein A is such that there is formed together with the carbon atom shown a five membered unsaturated heterocyclic ring having one nitrogen atom, one sulphur or oxygen atom and three carbon atoms, said unsaturated heterocyclic ring being thiazole, isothiazole, onazole or isoxazole, and Y is oxygen or sulphur (sulphur is preferred) are exemplified by the following examples.

EXAMPLE 110

By the procedure of Example 1, using as the starting materials 2-hydroxymethylthiazole and 4-hydroxymethylthiazole, were produced the following intermediate amine salts:

2-[(2-aminoethyl)thiomethyl]thiazole dihydrobromide, m.p. 144°–147.5° C.
4-[(2-aminoethyl)thiomethyl]thiazole dihydrobromide, m.p. 197°–203° C.

These intermediate salts were reacted with methyl isothiocyanate by the procedure of Example 1 to give:
N-methyl-N'-[2-(2-thiazolylmethylthio)ethyl]thiourea, recrystallised from isopropyl acetate, m.p. 114°–116° C. (Found: C, 38.8; H, 5.4; N, 17.0; S, 38.9. $C_8H_{13}N_3S_3$ requires: C, 38.8; H, 5.3; N, 17.0; S, 38.9)
N-methyl-N'-[2-(4-thiazolylmethylthio)ethyl]thiourea, recrystallised from isopropyl acetate/isopropanol, m.p. 78°–80.5° C. (Found: C, 38.8; H, 5.3; N, 17.2; S, 38.7. $C_8H_{13}N_3S_3$ requires: C, 38.8; H, 5.3; N, 17.0; S, 38.9)

EXAMPLE 111

By the procedure of Example 21(i), using 2-mercaptothiazole as the starting material, the intermediate amine salt, 2-(3-aminopropylthio)thiazole dihydrobromide, m.p. 175°–178° C., was prepared.

This intermediate amine salt was reacted with methyl isothiocyanate by the procedure of Example 21(ii) to give N-methyl-N'-[3-(2-thiazolylthio)propyl]thiourea, recrystallised from water, m.p. 67°–68° C. (Found: C, 38.6; H, 5.3; N, 16.9; S, 38.9. $C_8H_{13}N_3S_3$ requires: C, 38.8; H, 5.3; N, 17.0; S, 38.9).

EXAMPLE 112

N-Methyl-N'-[2-(5-thiazolylmethylthio)ethyl]thiourea

The reaction of 5-hydroxymethylthiazole (2.01 g.) with cysteamine hydrochloride (1.99 g.) in aqueous hydrobromic acid by the method described in Example 1(i)(a) gave 5-[(2-aminoethyl)thiomethyl]thiazole dihydrobromide (4.85 g.), m.p. 191°–194° (from methanol).

The reaction of 5-[(2-aminoethyl)thiomethyl]thiazole (2.24 g.) with methyl isothiocyanate (0.94 g.) in ethanol (10 ml.) gave a thiourea which was purified by chromatography on a column of silica gel with ethyl acetate as eluant. Recrystallisation from isopropyl acetate-methyl ethyl ketone-ether gave N-methyl-N'-[2-(5-thiazolylmethylthio)ethyl]thiourea (2.1 g.), m.p. 86°–88°. (Found: C, 38.6; H, 5.4; N, 16.9; S, 38.6. $C_8H_{13}N_3S_3$ requires: C, 38.8; H, 5.3; N, 17.0; S, 38.9).

EXAMPLE 113

N-Methyl-N'-[2-((2-amino-4-thiazolyl)methylthio)ethyl]thiourea

A mixture of 2-amino-4-chloromethylthiazole hydrochloride (9.0 g.) and cysteamine hydrochloride (5.53 g.) in acetic acid (100 ml.) was heated under reflux for 18 hours. The crude product obtained after concentration was treated with picric acid in ethanol to afford 2-amino-4-[(2-aminoethyl)thiomethyl]thiazole dipicrate, m.p. approximately 200°–210° (from ethanol).

The picrate was converted into the free base by addition of hydrochloric acid, removal of picric acid by toluene extraction, basification with potassium carbonate and extraction of the aqueous residue with ethanol-ether. Reaction of the base (1.89 g.) with methyl isothiocyanate (0.73 g.) in ethanol (10 ml.) in the usual way gave the crude thiourea. Chromatography on a column of silica gel with ethyl acetate as the eluant, followed by recrystallisation from isopropyl alcohol-isopropyl acetate gave N-methyl-N'-[2-((2-amino-4-thiazolyl)methylthio)ethyl]thiourea (1.0 g.), m.p. 136°–140°. (Found: C, 37.1; H, 5.5; N, 20.8; S, 36.3. $C_8H_{14}N_4S_3$ requires: C, 36.6; H, 5.4; H, 21.3; S, 36.7).

EXAMPLE 114

Using the following thiazoles as starting materials in the procedure of Example 1:

2-hydroxymethyl-4-methylthiazole
4-chloromethyl-2-methylthiazole
2-chloro-4-chloromethylthiazole
2-bromomethyl-4,5-dimethylthiazole
4-ethyl-2-hydroxymethyl-5-methylthiazole
the products are, respectively:
N-methyl-N'-[2-((4-methyl-2-thiazolyl)methylthio)ethyl]-thiourea
N-methyl-N'-[2-((2-methyl-4-thiazolyl)methylthio)ethyl]-thiourea
N-methyl-N'-[2-((2-chloro-4-thiazolyl)methylthio)ethyl]-thiourea
N-methyl-N'-[2-((4,5-dimethyl-2-thiazolyl)methylthio)-ethyl]thiourea
N-methyl-N'-[2-((4-ethyl-5-methyl-2-thiazolyl)methylthio)-ethyl]thiourea.

By the same procedure, using ethyl isothiocyanate the corresponding N-ethyl thioureas are prepared.

EXAMPLE 115

2-Benzyl-4-thiazolecarboxylic acid is converted to the methyl ester and the ester is reduced with lithium aluminium hydride in tetrahydrofurann to give 2-benzyl-4-hydroxymethylthiazole. Using this compound as the starting material in the procedure of Example 1 gives N-methyl-N'-[2-((2-benzyl-4-thiazolyl)methylthio)ethyl]-thiourea.

By the same procedure, from the following compounds:
2,4-thiazoledicarboxylic acid
2-hydroxy-4-thiazolecarboxylic acid
the following products are obtained, respectively:
2,4-bis-[2-(N-methylthioureido)ethylthiomethyl]-triazole
N-methyl-N'-[2-((2-hydroxy-4-thiazolyl)methylthio)ethyl]thiourea Reduction of 5-bromo-4-methyl-2-thiazolecarboxylic acid with diborane yields 5-bromo-4-methyl-2-hydroxymethylthiazole which by the procedure of Example 1 may be converted to N-methyl-N'-[2-((5-bromo-4-methyl-2-thiazolyl)methylthio)-ethyl]thiourea.

EXAMPLE 116

N-Methyl-N'-[2-(4-thiazolylmethoxy)propyl]thiourea

By the same procedure of Example 28, using as the starting material 4-chloromethylthiazole (prepared by reacting 4-hydroxymethylthiazole with thionyl chloride) the title compound is prepared.

EXAMPLE 117

N-Methyl-N'-[2-(2-(4-thiazolyl)ethyl)thioethyl]thiourea

By the procedure of Example 17, using 4-(2-chloroethyl)thiazole, the title compound is prepared.

EXAMPLE 118

N-Methyl-N'-[2-(2-thiazolylmethylthio)ethyl]urea

By the procedure of Example 24, 2-[(2-aminoethyl)thiomethyl]thiazole is reacted with methyl isocyanate to give the title compound, m.p. 65°–65.5° (from isopropyl acetate). (Found: C, 41.7; H, 5.6; N, 18.3; S, 28.1. $C_8H_{13}N_3S_2O$ requires: C, 41.5; H, 5.7; N, 18.2; S, 27.7).

EXAMPLE 119

By the procedure of Example 18, 2-[(2-aminoethyl)-thiomethyl]thiazole is reacted with benzoyl isothiocyanate to give N-benzoyl-N'-[2-(2-thiazolymethylthio)ethyl]thiourea. Removing the benzoyl group by the procedure of Example 18 gives N-[2-(2-thiazolylmethylthio)ethyl]thiourea. Treating this compound with hydrobromic acid gives the hydrobromide salt.

EXAMPLE 120

N-(2-Dimethylaminoethyl)-N'-[2-(2-thiazolylmethylthio)ethyl]-thiourea

Treatment of 2-[(2-aminoethyl)thiomethyl]thiazole with 2-dimethylaminoethyl isothiocyanate by the procedure of Example 1 gives the title compound.

EXAMPLE 121

| Ingredients | Amounts |
| --- | --- |
| N-Methyl-N'-[2-(2-thiazolylmethylthio)ethyl]-thiourea | 200 mg. |
| Lactose | 100 mg. |

The ingredients are screened, mixed and filled into a hard gelatin capsule.

EXAMPLE 122

N-Methyl-N'-[2-(3-isothiazolylmethylthio)ethyl]thiourea.

A solution was prepared by the gradual addition of cysteamine hydrochloride (2.03 g.) to sodium (0.83 g.) dissolved in ethanol (50 ml.) with stirring at 0° under a nitrogen atmosphere. After stirring for 2 hours at 0°, 3-bromomethylisothiazole (3.2 g.) was added dropwise over 15 minutes at 0°, the reaction mixture subsequently being set aside overnight at room temperature. Following acidification to pH 3.5 with hydrochloric acid, concentration and re-evaporation with ethanol, the residue was dissolved in ethanol, filtered and concentrated to yield 3-[(2-aminoethyl)thiomethyl]isothiazole hydrochloride (3.5 g.). This was converted directly to the free base by treatment with aqueous potassium carbonate and extraction with ether. The extracts were dried over magnesium sulphate, filtered and concentrated to yield the amine base as an oil (1.56 g.). The amine was dissolved in ethanol (10 ml.), methyl isothiocyanate (0.66 g.) added, and the solution heated under reflux for 30 minutes. Concentration, followed by purification of the crude product by chromatography on a column of silica gel with ethyl acetate as eluant followed by chromatography on a column of alumina with benzene/ethyl acetate as eluant gave N-methyl-N'-[2-(3-isothiazolylmethylthio)ethyl]thiourea. (Found: C, 38.9; H, 5.4 N, 16.5; S, 38.3. $C_8H_{13}N_3S_3$ requires: C, 38.8; H, 5.3; N, 17.0; S, 38.9).

EXAMPLE 123

N-Methyl-N'-[2-((4-bromo-3-isothiazolyl)methylthio)ethyl]-thiourea

The reaction of 4-bromo-3-(bromomethyl)isothiazole (8.5 g.) with cysteamine (from cysteamine hydrochloride (3.76 g.)) was performed under conditions similar to those described in Example 122. From the reaction there was obtained 4-bromo-3-[(2-aminoethyl)thiomethyl]isothiazole hydrobromide, which, following recrystallisation from ethanol-ether and acetonitrile, gave needles (4.05 g.), m.p. 111°–112°. The amine base (2.73 g.) was isolated by basification with sodium hydroxide and extraction with chloroform and then dissolved in ethanol and treated with methyl isothiocyanate (0.78 g.). The solution was heated under reflux for 30 minutes, concentrated and the residue triturated with ether to yield the crystalline thiourea (2.9 g.) m.p. 60°–61°. Recrystallisation from isopropyl acetate gave N-methyl-N'-[2-((4-bromo-3-isothiazolyl)-methylthio)ethyl]thiourea (2.3 g.) as needles, m.p. 62°–63°. (Found: C, 29.5; H, 3.8; N, 12.9; Br, 24.6; S, 29.3. $C_8H_{12}BrN_3S_3$ requires: C, 29.5; H, 3.7; N, 12.9; Br, 24.5; S, 29.5).

EXAMPLE 124

Using the following halomethylisothiazoles as starting materials in the procedure of Example 122:
3-bromomethyl-4-chloroisothiazole
4-bromo-5-chloromethyl-3-methylisothiazole
the products are, respectively:
N-methyl-N'-[2-((4-chloro-3-isothiazolyl)methylthio)ethyl]thiourea
N-methyl-N'-[2-((4-bromo-3-methyl-5-isothiazolyl)-methylthio)ethyl]thiourea.

By the same procedure, using ethyl isothiocyanate the corresponding N-ethyl thiourea compounds are obtained.

EXAMPLE 125

Reacting 4-hydroxymethyl-3-methylisothiazole (3.0 g.) with cysteamine hydrochloride (2.8 g.) in 48% aqueous hydrobromic acid (50 ml.) by the procedure of Example 1 gives 3-methyl-4-[(2-aminoethyl)thiomethyl]-isothiazole hydrobromide. The base is obtained by basifying with aqueous potassium carbonate, extracting with chloroform, drying the extracts over magnesium sulphate and concentrating. Reacting the amine (5.0 g.) with methyl isothiocyanate (1.94 g.) in ethanol (25 ml.) under reflux for 30 minutes and purifying the product on a column of alumina with benzene as eluant gives N-methyl-N'-[2-(3-methyl-4-isothiazolylmethylthio)ethyl]thiourea. (Found: C, 40.8; H, 5.9; N, 16.1; S, 36.4. $C_9H_{15}N_3S_3$ requires: C, 41.3; H, 5.8; N, 16.1; S, 36.8).

3,5-Dimethyl-4-isothiazolecarboxylic acid is converted to the ethyl ester and the ester is reduced with lithium aluminium hydride in tetrahydrofuran to give 4-hydroxymethyl-3,5-dimethylisothiazole. Using this hydroxymethyl compound as the starting material for the above process gives N-methyl-N'-[2-((3,5-dimethyl-4-isothiazolyl)methylthio)ethyl]thiourea.

Similarly, using 3,5-isothiazoledicarboxylic acid the product is 3,5-bis-[2-(N-methylthioureido)ethylthiomethyl]isothiazole.

EXAMPLE 126

N-Methyl-N'-[2-((4-bromo-3-isothiazolyl)methylthio)ethyl]urea

Reacting 4-bromo-3-[(2-aminoethyl)thiomethyl]isothiazole with methyl isocyanate by the procedure of Example 24 gives the title compound.

EXAMPLE 127

N-Methyl-N'-[3-(3-isothiazolylmethoxy)propyl]thiourea

Using 3-bromomethylisothiazole in the procedure of Example 28 gives the title compound.

EXAMPLE 128

N-Methyl-N'-[2-(2-(3-isothiazolyl)ethyl)thioethyl]thiourea

3-Isothiazoleacetic acid is converted to the methyl ester and the ester is reduced with lithium aluminium hydride in tetrahydrofuran to give 3-(2-hydroxyethyl)isothiazole. Reacting this hydroxyethyl compound with thionyl chloride gives 3-(12-chloroethyl)isothiazole. Using 3-(2-chloroethyl)isothiazole in the procedure of Example 17 gives the title compound.

EXAMPLE 129

By the procedure of Example 18, 3-[(2-aminoethyl)thiomethyl]isothiazole is reacted with benzoyl isothiocyanate to give N-benzoyl-N'-[2-(3-isothiazolylmethylthio)ethyl]-thiourea. Removing the benzoyl group by the procedure of Example 18 gives N-[2-(3-isothiazolylmethylthio)ethyl]thiourea.

EXAMPLE 130

N-(2-Dimethylaminoethyl)-N'-[2-(3-isothiazolylmethylthio)-ethyl]thiourea

Treatment of 3-[(2-aminoethyl)thiomethyl]isothiazole with 2-dimethylaminoethyl isothiocyanate by the procedure of Example 1 gives the title compound.

EXAMPLE 131

| Ingredients | Amounts |
| --- | --- |
| N-Methyl-N'-[2-(3-isothiazolylmethylthio)ethyl]thiourea | 200 mg. |
| Lactose | 100 mg. |

The ingredients are mixed and filled into a hard gelatin capsule.

EXAMPLE 132

N-Methyl-N'-[3-(2-oxazolylthio)propyl]thiourea i. Hydrochloric acid (90 ml.) was added to potassium thiocyanate in ethanol (1.8 l.) with stirring. Following filtration from inorganic material, glycollaldehyde (35.9 g.) was added and the resulting solution was heated under reflux for 24 hours. Concentration, followed by cooling afforded a white solid, which following recrystallisation from ethanol afforded oxazole-2-thiol (30 g.) m.p. 143°–144°.

ii. 3-Bromopropylphthalimide (13.4 g.) was added to a stirred solution of sodium ethoxide (from 1.15 g. sodium) and oxazole-2-thiol (5.1 g.) in ethanol (100 ml.). The resultant solution was heated under reflux for 2.5 hours and concentrated under reduced pressure. The residue was triturated with water (100 ml.) to afford 2-(3-phthalimidopropylthio)oxazole (14 g.), m.p. 101°. Recrystallisation from ethanol gave the pure oxazole, m.p. 102°–103°.

iii. Hydrazine hydride (5.3 g.) was added carefully to a solution of 2-(3-phthalimidopropylthio)oxazole (10. g.) in ethanol (173 ml.) with stirring. The solution was then heated under reflux for 25 minutes. After cooling, and filtration from phthalhydrazide, the filtrate was concentrated under reduced pressure and the residue was re-evaporated with ethanol to yield crude 2-(3-aminopropylthio)oxazole which was washed twice with ether and dissolved in ethanol (60 ml.). Methyl isothiocyanate (2.54 g.) was added and the solution was heated under reflux for 30 minutes. Following cooling and filtration from insoluble material, the filtrate was concentrated to an oil which was chromatographed on a column of silica gel with ethyl acetate as eluant. The product obtained crystallised from ethanol-ether-n-hexane to give N-methyl-N'-[3-(2-oxazolylthio)propyl]thiourea (2.4 g.), m.p. 43°–45°. (Found: C, 41.7; H, 5.9; N, 18.3; S, 27.5. $C_8H_{13}N_3OS_2$ requires: C, 41.5; H, 5.7; N 18.2; S, 27.7).

EXAMPLE 133

N-Methyl-N'-[3-(4-methyl-2-oxazolyl)thiopropyl]thiourea i. The reaction of 4-methyloxazole-2-thiol (5.8 g.) with 3-bromopropylphthalimide (13.4 g.) using the conditions described in Example 132 afforded 4-methyl-2-(3-phthalimidopropylthio)oxazole (14 g.), m.p. 92°–93° (ethanol-ether).

ii. Treatment of the phthalimide compound (3.0 g.) with hydrazine (1.53 g.) followed by reaction of the product directly with methyl isothiocyanate (0.73 g.) using the conditions described in Example 132 afforded N-methyl-N'-[3-(4-methyl-2-oxazolyl)thiopropyl]thiourea (1.0 g.). m.p. 73°–74° (from ethanol-n-hexane). (Found: C, 44.0; H, 6.2; N, 17.1; S, 25.9. $C_9H_{15}N_3OS_2$ requires: C, 44.1; H, 6.2; N, 17.1; S, 26.1).

EXAMPLE 134

Using the following 2-(chloroethyl)oxazoles as starting materials in the procedure of Example 17:
5-(2-chloroethyl)-4-methyloxazole
5-(2-chloroethyl)-4-trifluoromethyloxazole
the products are, respectively:
N-methyl-N'-[2-(2-(4-methyl-5-oxazolyl)ethyl)thioethyl]thiourea
N-methyl-N'-[2-(2-(4-trifluoromethyl-5-oxazolyl)ethyl)-thioethyl]thiourea.

Also, using 2-amino-5-(2-chloroethyl)oxazole (prepared by reacting 2-amino-5-(2-hydroxyethyl)oxazole with thionyl chloride) in the procedure of Example 17 gives N-methyl-N'-[2-(2-(2-amino-5-oxazolyl)ethyl)-thioethyl]thiourea.

EXAMPLE 135

Methyl 5-benzyl-4-oxazolecarboxylate is reduced with lithium aluminium hydride in tetrahydrofuran to give 5-benzyl-4-hydroxymethyloxazole, which on reaction with thionyl chloride is converted to 5-benzyl-4-chloromethyloxazole.

Using 5-benzyl-4-chloromethyloxazole as the staring material, N-methyl-N'-[2-((5-benzyl-4-oxazolyl)- methylthio)ethyl]thiourea is prepared by the procedure of Example 1(i)(b) and (ii).

By the same procedure, using 2,5-dimethyl-4-oxazolecarboxylic acid, the product is N-methyl-N'-[2-((2,5-dimethyl-4-oxazolyl)methylthio)ethyl]thiourea.

Also, by the same procedure, using 4,5-oxazolediacarboxylic acid, 4,5-bis-[2-(N-methylthioureido)ethylthiomethyl]oxazole is prepared.

Reduction of 5-chloro-2-methyl-4-oxazolecarboxylic acid with diborane to the corresponding 4-hydroxymethyl compound, conversion of this to the 4-chloromethyl compound and using this chloromethyl compound as the starting material gives, by the procedure of Example 1(i)(b) and (ii), N-methyl-N'-[2-((5-chloro-2-methyl-4-oxazolyl)methylthio)ethyl]thiourea.

By the same procedure, using 5-chloro-4-chloromethyl-2-methyloxazole (prepared from the corresponding 4-carboxylic acid by the diborane reduction procedure described above) and 3-phthalimidopropanethiol, the product is N-methyl-N'-[3-((5-chloro-2-methyl-4-oxazolyl)methylthio)-propyl]thiourea.

EXAMPLE 136

N-Methyl-N'-[2-((4-methyl-5-oxazolyl methylthio)ethyl]urea

By the procedure of Example 1(i)(b), using 4-methyl-5-chloromethyloxazole as the starting material, 5-](2-aminoethyl)thiomethyl]-4-methyloxazole is prepared.

Reacting 5-[(2-aminoethyl)thiomethyl]-4-methyloxazole with methyl isocyanate by the procedure of Example 24 gives the title compound.

EXAMPLE 137

N-Methyl-N'-[2-((5-methyl-4-oxazolyl)methoxy)ethyl]thiourea

By the procedure of Example 38, 5-chloromethyl-4-methyloxazole is converted to 4-(2-chloroethoxymethyl)-5-methyloxazole.

Using 4-(2-chloroethoxymethyl)-5-methyloxazole hydrochloride (prepared by treating the base with hydrochloric acid) in the procedure of Example 23 gives the title compound.

EXAMPLE 138

5-[(2-Aminoethyl)thiomethyl]-4-methyloxazole is reacted with benzoyl isothiocyanate by the procedure of Example 18 to give N-benzoyl-N'-[2-((4-methyl-5-oxazolyl)-methylthio)ethyl]thiourea. Removing the benzoyl group by the procedure of Example 18 gives N-[2-((4-methyl-5-oxazolyl)methylthio)ethyl]thiourea.

Also, reacting 5-[(2-aminoethyl)thiomethyl]-4-methyloxazole with ethyl isothiocyanate by the procedure of Example 1 gives N-ethyl-N'-[2-((4-methyl-5-oxazolyl)-methylthio)ethyl]thiourea.

EXAMPLE 139

N-(2-Dimethylaminoethyl)-N'-[2-((4-methyl-5-oxazolyl)methyl-thio)ethyl]thiourea

5-[(2-Aminoethyl)thiomethyl]-4-methyloxazole is reacted with 2-dimethylaminoethyl isothiocyanate by the procedure of Example 1 to give the title compound.

EXAMPLE 140

| Ingredients | Amounts |
| --- | --- |
| N-Methyl-N'-[3-(2-oxazolylthio)propyl]-thiourea | 150 mg. |
| Sucrose | 75 mg. |
| Starch | 25 mg. |
| Talc | 5 mg. |
| Stearic acid | 2 mg. |

The ingredients are mixed and filled into a hard gelatin capsule.

EXAMPLE 141

| Ingredients | Amounts |
| --- | --- |
| N-Methyl-N'-[3-(4-methyl-2-oxazolyl)-thiopropyl]thiourea | 200 mg. |
| Lactose | 100 mg. |

The ingredients are mixed and filled into a hard gelatin capsule.

EXAMPLE 142

N-Methyl-N'-[2-(3-isoxazolylmethylthio)ethyl]thiourea a. A solution of 3-chloromethylisoxazole (5.8 g.) and cysteamine hydrochloride (6.25 g.) in aqueous hydrobromic acid (48%, 100 ml.) was heated under reflux for 6 hours. Concentration in the presence of water and subsequently n-propanol, followed by recrystallisation of the residue from isopropyl alcohol-ethanol afforded 3-[(2-aminoethyl)-thiomethyl]isoxazole hydrobromide, m.p. 131°–133°. (Found: Br, 33.6; S, 13.7. $C_6H_{10}N_2OS.HBr$ requires: Br, 33.4; S, 13.4).

b. A solution of 3-[(2-aminoethyl)thiomethyl]isoxazole (2.44 g.) extracted from the hydrobromide and potassium carbonate with ether-ethanol (3:1) and methyl isothiocyanate (1.36 g.) in absolute ethanol (40 ml.) was heated under reflux for 1.5 hours. Concentration followed by chromatographic purification on a column of silica gel was ether as eluant afforded N-methyl-N'-[2-(3-isoxazolyl-methylthio)ethyl]thiourea as a colorless oil (2.5 g.). (Found: C, 41.3; H, 6.2; N, 18.2; S, 27.3. $C_8H_{13}N_2O_2S$ requires C, 41.5; H, 5.7; N, 18.2; S, 27.7).

EXAMPLE 143

Using the following chloromethylisoxazoles (prepared from the corresponding hydroxymethylisoxazoles by treatment thereof with thionyl chloride) as starting materials in the procedure of Example 142:
  3-chloromethyl-5-methylisoxazole
  3-bromo-5-chloromethylisoxazole
  4-chloromethyl-3,5-dimethylisoxazole
  4-(2-chloroethyl)-5-methylisoxazole
the products are, respectively:
  N-methyl-N'-[2-(5-methyl-3-isoxazolylmethylthio)ethyl]-thiourea
  N-methyl-N'-[2-(3-bromo-5-isoxazolylmethylthio)ethyl]-thiourea
  N-methyl-N'-[2-(3,5-dimethyl-4-isoxazolylmethylthio)ethyl]-thiourea
  N-methyl-N'-[2-(2-(5-methyl-4-isoxazolyl)ethylthio)ethyl]-thiourea.

EXAMPLE 144

Using, in the procedure of Example 142, 3-mercaptopropylamine in place of cysteamine, the product is N-methyl N'-[3-(3-isoxazolylmethylthio)propyl]thiourea.

EXAMPLE 145

Reaction of 3-[(2-aminoethyl)thiomethyl]isoxazole methyl isocyanate by the procedure of Example 24 gives N-methyl-N'[2-(3-isoxazolylmethylthio)ethyl]urea.

EXAMPLE 146

By the procedure of Example 38, 3-chloromethylisoxazole is converted to 3-(2-chloroethoxymethyl)isoxazole which is then reacted with methyl isothiocyanate to give N-methyl-N'-[2-(3-isoxazolylmethoxy)ethyl]thiourea.

EXAMPLE 147

3-(2-Aminoethyl)thiomethyl]isoxazole is reacted with benzoyl isothiocyanate by the procedure of Example 18 to give N-benzoyl-N'-[2-(3-isoxazolylmethylthio)ethyl-thiourea. Removing the benzoyl group by the procedure of Example 18 gives N-[2-(3-isoxazolylmethylthio)ethyl]thiourea.

EXAMPLE 148

Reaction of 3-[(2-aminoethyl)thiomethyl]isoxazole by the procedure of Example 142(b) with the following isothiocyanates:
 ethyl isothiocyanate
 propyl isothiocyanate
 2-dimethylaminoethyl isothiocyanate
gives the follwing products, respectively:
 N-ethyl-N'-[2-(3-isoxazolylmethylthio)ethyl]thiourea
 N-propyl-N'-[2-(3-isoxazolylmethylthio)ethyl]thiourea
 N-(2-dimethylaminoethyl)-N'-[2-(3-isoxazolylmethylthio)ethyl]thiourea.

EXAMPLE 149

| Ingredients | Amounts |
| --- | --- |
| N-Methyl-N'-[2-(3-isoxazolyl-methylthio)ethyl]thiourea | 200 mg. |
| Lactose | 100 mg. |

The ingredients are mixed and filled into a hard gelatin capsule.

Compounds of formula I wherein A is such that there is formed together with the carbon atom shown a five membered unsaturated heterocyclic ring having one nitrogen atom, one sulphur or oxygen atom and three carbon atoms, said unsaturated heterocyclic ring being thiazole, isothiazole, oxazole or isoxazole, and Y is NH are exemplified by the following examples.

EXAMPLE 150

Using in the procedure of Example 40, the following halomethylthiazoles (which may be prepared by treating the hydroxymethylthiazoles with a thionyl halide):

2-chloromethylthiazole
4-chloromethylthiazole
5-chloromethylthiazole
2-amino-4-chloromethylthiazole
2-chloromethyl-4-methylthiazole
2-chloro-4-chloromethylthiazole
2-bromomethyl-4,5-dimethylthiazole
2-benzyl-4-chloromethylthiazole
2,4-di(chloromethyl)thiazole
5-bromo-2-chloromethyl-4-methylthiazole
4-chloromethyl-2-hydroxythiazole the products are, respectively:
 N-methyl-N'-[2-(2-thiazolylmethylamino)ethyl]thiourea
 N-methyl-N'-[2-(4-thiazolylmethylamino)ethyl]thiourea
 N-methyl-N'-[2-(5-thiazolylmethylamino)ethyl]thiourea
 N-methyl-N'-[2-((2-amino-4-thiazolyl)methylamino)-ethyl]thiourea
 N-methyl-N'[2-((4-methyl-2-thiazolyl)methylamino)-ethyl]thiourea
 N-methyl-N'-[2-((2-chloro-4-thiazolyl)methylamino)-ethyl]thiourea
 N-methyl-N'[2-((4,5-dimethyl-2-thiazolyl)methylamino)-ethyl]thiourea
 N-methyl-N'-[2-((2-benzyl-4-thiazolyl)methylamino)ethyl]-thiourea
 2,4-bis-[2-(N-methylthioureido)ethylaminomethyl]-thiazole
 N-methyl-N'-[2-((5-bromo-4-methyl-2-thiazolyl)-methyl-amino)ethyl]thiourea
 N-methyl-N'-[2-((2-hydroxy-4-thiazolyl)methylamino)-ethyl]thiourea.

Similarly, using ethyl isothiocyanate, the corresponding N-ethyl compounds are obtained.

Treatment of N-methyl-N'-[2-(2-thiazolylmethylamino)ethyl]thiourea with hydrochloric acid gives the hydrochloride salt. Similarly, treatment with maleic acid in ethanol gives the maleate salt.

Als , using in the procedure of Example 40, 2-chloromethylthiazole and 1,3-diaminopropane as the starting materials, the product is N-methyl-N'-[3-(2-thiazolylmethylamino)propyl]thiourea.

EXAMPLE 151

N-Methyl-N'-[2-(2-(4-thiazolyl)ethyl)aminoethyl]thiourea

Using 4-(2-chloroethyl)thiazole in the procedure of Example 40 gives the title compound

EXAMPLE 152

N-Methyl-N'-[3-(2-thiazolylamino)propyl]thiourea

Using 2-aminothiazole as the starting material in the procedure of Example 53 gives the title compound.

EXAMPLE 153

N-Methyl-N'-[2-(2-thiazolylmethylamino)ethyl]urea

N-(2-Thiazolylmethyl)ethylenediamine, prepared by reacting ethylenediamine with 2-chloromethylthiazole by the procedure of Example 40, is reacted with methyl isocyanate by the procedure of Example 24 to give, after concentrating and separating by column chromatography, the title compound.

EXAMPLE 154

By the procedure of Example 46, reacting 2-(3-aminopropylamino)thiazole prepared from 2-aminothiazole by the method of Example 53)with benzoyl isothiocyanate gives N-benzoyl-N'-[3-(2-thiazolylamino)propyl]thiourea. Removing the benzoyl group by the procedure of Example 46 gives N-[3-(2-thiazolylamino)propyl]thiourea.

By the same procedure, using 3-aminoisothiazole, N-benzoyl-N'-[3-(3-isothiazolylamino)propyl]thiourea is prepared and the benzoyl group is removed to give N-[3-(3-isothiazolylamino)propyl]thiourea.

EXAMPLE 155

N-(2-Diamethylaminoethyl)-N'-[2-(2-thiazolylmethylamino)ethyl]-thiourea

Treating N-(2-thiazolylmethyl)ethylenediamine with 2-dimethylaminoethyl isothiocyanate by the procedure of Example 40, then concentrating and separating by column chromatography gives the title compound.

EXAMPLE 156

| Ingredients | Amounts |
| --- | --- |
| N-Methyl-N'-[2-(2-thiazolylmethylamino)-ethyl]thiourea | 200 mg. |
| Lactose | 100 mg. |

The ingredients are mixed and filled into a hard gelatin capsule.

EXAMPLE 157

Using in the procedure of Example 40(a), the following haloalkylisothiazoles:

3-bromomethylisothiazole
4-bromo-3-bromomethylisothiazole
5-chloro-3-bromomethylisothiazole
4-bromo-5-chloromethyl-3-methylisothiazole
4-chloromethyl-3-methylisothiazole
4-bromomethyl-3,5-dimethylisothiazole
3,5-di(bromomethyl)isothiazole
3-(2-chloroethyl)isothiazole the products are, respectively:
N-methyl-N'-[2-(3-isothiazolylmethylamino)ethyl]-thiourea
N-methyl-N'-[2-((4-bromo-3-isothiazolyl)methylamino)-ethyl]thiourea
N-methyl-N'-[2-((5-chloro-3-isothiazolyl)methylamino)-ethyl]thiourea
N-methyl-N'-[2-((4-bromo-3-methyl-5-isothiazolyl)-methylamino)ethyl]thiourea
N-methyl-N'-[2-((3-methyl-4-isothiazolyl)me-, thylamino)-ethyl]thiourea
N-methyl-N'-[2-((3.5-dimethyl-4-isothiazolyl)methylamino)ethyl]thiourea
3,5-bis-[2-(N-methylthioureido)ethylaminomethyl-]isothiazole
N-methyl-N'-[2-(2-(3-isothiazolyl)ethyl)aminoethyl]-thiourea.

Also, by the preocedure of Example 40(a), using ethyl isothiocyanate, the corresponding N-ethyl compounds are prepared.

IN addition, using in the procedure of Example 40(a), 3-bromomethylisothiazole and 1,3-diaminopropane as the starting materials, the product is N-methyl-N'-[3-(3-isothiaziolylmethylamino)propyl]thiourea.

EXAMPLE 158

N-Methyl-N'-[2-(3-isothiazolylmethylamino)ethyl-]urea

N-(3-Isothiazolylmethyl)ethylenediamine, prepared by reacting ethylenediamine with 3-bromomethylisothiazole by the procedure of Example 40(a), is reacted with methyl isocyanate by the procedure of Example 24 to give, after concenrating and separating by column chromatography, the title compound.

EXAMPLE 159

By the procedure of Example 40(a) (ii), N-(3-isothiazolylmethyl)ethylenediamine is reacted with 2-dimethylaminoethyl isothiocyanate to give N-(2-dimethylaminoethyl)-N'-[2-(3-isothiazolylmethylamino)ethyl]thiourea. Reacting with hydrobromic acid gives the hydrobromide salt.

EXAMPLE 160

| Ingredients | Amounts |
| --- | --- |
| N-Methyl-N'-[2-(3-isothiazolylmethyl-amino)ethyl]thiourea | 200 mg. |
| Sucrose | 70 mg. |
| Starch | 25 mg. |
| Talc | 5 mg. |
| Stearic acid | 2 mg. |

The ingredients are mixed and filled into a hard gelatin capsule.

EXAMPLE 161

Using, in the procedure of Example 40(a), the following haloalkyloxazoles:

5-(2-chloroethyl)-4-methyloxazole
5-(2-chloroethyl)-4-trifluoromethyloxazole
2-amino-5-(2-chloroethyl)oxazole the products are, respectively:
N-methyl-N'-[2-(2-(4-methyl-5-oxazolyl)ethyl)aminoethyl]thiourea
N-methyl-N'-[2-(2-(4-trifluoromethyl-5-oxazolyl)ethyl)-aminoethyl]thiourea
N-methyl-N'-[2-(2-(2-amino-5-oxazolyl)ethyl)aminoethyl]-thiourea.

By the same procedure, using ethyl isothiocyanate, the corresponding N-ethyl compounds are prepared.

EXAMPLE 162

Using 5-benzyl-4-chloromethyloxazole (prepared by converting 5benzyl-4-oxazolecarboxylic acid to the methyl ester, then reducing the ester with lithium aluminium hydride in tetrahydrofuran and treating the resulting 5-benzyl-4-hydroxymethyloxazole with thionyl chloride) in the procedure of Example 40(a), the product is N-methyl-N'-[2-((5-benzyl-4-oxazolyl)methylamino)ethyl]thiourea.

By the same procedure, using the following as starting materials:

2,5-dimethyl-4-oxazolecarboxylic acid
4,5-oxazoledicarboxylic acid the following products are obtained, respectively:
N-methyl-N'-[2-((2,5-dimethyl-4-oxazolyl)methylamino)-ethyl]thiourea 4,5-bis-[2-(N-methylthioureido)ethylaminomethyl-]oxazole.

EXAMPLE 163

Reduction of 5-chloro-2-methyl-4-oxazolecarboxylic acid with diborane and conversion of the resulting 4-hydroxymethyl compound with thionyl chloride to the corresponding chloromethyl analog which is then used as the starting material in the process of Example 40(a) gives N-methyl-N'-[2-((5-chloro-2-methyl-4-oxazolyl)methylamino)ethyl]thiourea.

Using in the procedure of Example 40(a), 5-chloro-4-chloromethyl-2-methyloxazole (prepared from the corresponding 4-carboxylic acid compound by the diborane reduction/thionyl chloride procedure described above) and 1,3-diaminopropane as the starting materials, the product is N-methyl-N'-[3-((5-chloro-2-methyl-4-oxazolyl)methylamino)propyl]thiourea.

EXAMPLE 164

N-(2-Dimethylaminoethyl)-N'-[2-(2-(4-methyl-5-oxazolyl)-ethyl)aminoethyl]thiourea By the procedure of Example 40(a)(ii), N-[2-(4-methyl-5-oxazolyl)ethyl]ethylenediamine [prepared by reacting ethylenediamine with 5-(2-chloroethyl)-4-methyloxazole] is reacted with 2-dimethylaminoethyl isothiocyanate to give the titel compound.

EXAMPLE 165

| Ingredients | Amounts |
| --- | --- |
| N-Methyl-N'-[2-(2-(4-methyl-5-oxazolyl)ethyl)-aminoethyl]thiourea | 200 mg. |
| Lactose | 100 mg. |

The ingredients are mixed and filled into a hard gelatin capsule.

EXAMPLE 166

Using, in the procedure of Example 40, the following chloroalkylisoxazoles:
3-chloromethylisoxazole
3-chloromethyl-5-methyloxazole
3-bromo-5-chloromethylisoxazole
4-chloromethyl-3,5-dimethylisoxazole
4-(2-chloroethyl)-5-methylisoxazole
the products are, respectively:
N-methyl-N'-[2-(3-isoxazolylmethylamino)ethyl]thiourea
N-methyl-N'-[2-(5-methyl-3-isoxazolylmethylamine)-ethyl]thiourea
N-methyl-N'-[2-(3-bromo-5-isoxazolylmethylamino)-ethyl]thiourea
N-methyl-N'-[2-(3,5-dimethyl-4-isoxazolylmethylamino)-ethyl]thiourea
N-methyl-N'-[2-(2-(5-methyl-4-isoxazolyl)ethylamino)-ethyl]thiourea.

EXAMPLE 167

Using in the procedure of Example 40, 3-chloromethylisoxazole and 1,3-diaminopropane as the starting materials, the product is N-methyl-N'-[3-(3-isoxazolylmethylamino)propyl]thiourea.

EXAMPLE 168

N-(3-Isoxazolylmethyl)ethylenediamine is reacted with methyl isocyanate by the procedure of Example 24 to give, after concentrating and separating by column chromatography, N-methyl-N'-[2-(3-isoxazolylmethylamino)-ethyl]urea.

EXAMPLE 169

By the procedure of Example 40(a)(ii), N-(3-isoxazolylmethyl)ethylenediamine is reacted with the following isothiocyanates:
ethyl isothiocyanate
propyl isothiocyanate
2-dimethylaminoethyl isothiocyanate
to give, respectively:
N-ethyl-N'-[2-(3-isoxazolylmethylamino)ethyl]thiourea    N-propyl-N'-[2-(3-isoxazolylmethylamino)ethyl]thiourea
N-2-dimethylaminoethyl)-N'-[2-(3-isoxazolylmethyl-amino)ethyl]thiourea.

EXAMPLE 170

| Ingredients | Amounts |
| --- | --- |
| N-Methyl-N'-[2-(3-isoxazolylmethylamino)-ethyl]thiourea | 200 mg. |
| Lactose | 100 mg. |

The ingredients are mixed and filled into a hard gelatin capsule.

Compounds of formula I wherein A is such that there is formed together with the carbon atom shown a triazole ring and Y is oxygen or sulphur (sulphur is preferred) are exemplified by the following examples.

EXAMPLE 171

N-Methyl-N'-[2-(3-(1,2,4-triazolyl)methylthio)ethyl]-thiourea

By the procedure of Example 1, 3-[(2-aminoethyl)-thiomethyl]-1,2,4-triazole dihydrobromide, m.p. 177°–179°, was prepared.

Reacting this intermediate salt with methyl isothiocyanate by the procedure of Example 1 gives N-methyl-N'-[2-(3-(1,2,4-triazolyl)methylthio)ethyl]thiourea, recrystallised from ethanol/ether, m.p. 97°–99° C. (Found: C, 36.1; H, 5.7; N, 30.1; S, 28.0. $C_7H_{13}N_5S_2$ requires: C, 36.3; H, 5.7; N, 30.3; S, 27.7).

EXAMPLE 172

N-Methyl-N'-[2-(4-methyl-3-(1,2,4-triazolyl)methylthio)-ethyl]thiourea

Ethoxyacetyl chloride (57 g.) was added slowly to a stirred solution of 4-methylthiosemicarbazide (53.5 g.) in dry pyridine (500 ml.) at 0°–5°. The mixture was allowed to attain room temperature and stirring was continued for 18 hours. Following concentration under reduced pressure the residue was treated with a solution of sodium (21.4 g.) in ethanol (500 ml.) and the mixture was heated under reflux for 24 hours. Following concentration and acidification with hydrochloric acid a solid was obtained. After partial concentration the solid was collected and recrystallised from ethyl acetate to give 3-ethoxymethyl-4-methyl-1,2,4-triazoline-5-thione (53 g.), m.p. 137°–138°.

The thione (44 g.) was desulphurised by slow addition to a solution prepared from nitric acid (75 ml.), water (150 ml.) and sodium nitrite (1.5 g.) at 15°–20°. Following subsequent basification with sodium carbonate and concentration, the residue was extracted with ethanol-ether 1:1 and distilled to afford 3-ethoxymethyl-4-methyl 1,2,4-triazole (30 g.), b.p. 154°–156°/0.05 mm. The above compound (15 g.) dissolved in 48% aqueous hydrobromic acid (150 ml.) was heated under reflux for 24 hours, concentrated to dryness and the residue obtained (a mixture of 4-methyl-3-bromomethyl-1,2,4-triazole and 4-methyl-3-hydroxymethyl-1,2,4-triazole) was used directly in the reaction with cysteamine hydrochloride and hydrobromic acid as described in Example 1 (i)(a) to give 3-(2-aminoethyl)-4-methyl-1,2,4-triazole dihydrobromide, m.p. 175°–177°.

Reaction of 3-(2-aminoethyl)-4-methyl-1,2,4-triazole dihydrobromide with methyl isothiocyanate by the procedure of Example 1(ii) gives N-methyl-N'-[2-(4-methyl-3-(1,2,4-triazolyl)methylthio)enthyl]thiourea, which is recrystallised from water, m.p. 154°–155°. (Found: C, 39.3; H, 6.0; N, 28.7; S, 26.2. $C_8H_{15}N_5S_2$ requires: C, 39.2; H, 6.2; N, 28.5; S, 26.1).

EXAMPLE 173

3,5-bis-[2-(N-Methylthioureido)ethylthiomethyl)]-1,2,4-triazole i. The reaction of 3,5-di(hydroxymethyl)-1,2,4-triazole (90 g.; obtained from 1,2,4-triazole and excess formaldehyde at elevated temperatures) with cysteamine hydrochloride (17.3 g.) by the procedure described in Example 1 (i)(a) afforded 3,5-bis-[(2-aminoethyl)thiomethyl]-1,2,4-triazole trihydrobromide (4.7 g.), m.p. 214°–215°.

ii. The reaction of 3,5-bis-[(2-aminoethyl)thiomethyl]-1,2,4-triazole (from 6.5 g. trihydrobromide) with methyl isothiocyanate (1.93 g.) afforded the bis-thiourea which was purified by passage through a column of silica gel with ethanol as eluant. Trituration with isopropyl acetate, followed by recrystallisation from ethanol-ether afforded 3,5-bis-[2-(N-methylthioureido)ethylthiomethyl]-1,2,4-triazole (0.9 g.), m.p. 133°–135°. (Found: C, 35.7; H, 5.9; N, 24.6. $C_{12}H_{23}N_7S_4$ 0.5 $H_2O$ requires: C, 35.8; H, 6.1; N, 24.3).

EXAMPLE 174

By the procedure of Example 1 using the following hydroxymethyl triazoles as starting materials:
2-benzyl-3-hydroxymethyl-1,2,4-triazole
3-amino-5-hydroxymethyl-1,2,4-triazole
3-bromo-5-hydroxymethyl-1,2,4-triazole
1-benzyl-4-hydroxymethyl-1,2,3-triazole
the products are, respectively:
N-methyl-N'-[2-(2-benzyl-3-(1,2,4-triazolyl)methylthio)-ethyl]thiourea
N-methyl-N'-[2-(3-amino-5-(1,2,4-triazolyl)methylthio)-ethyl]thiourea
N-methyl-N'-[2-(3-bromo-5-(1,2,4-triazolyl)methylthio)-ethyl]thiourea
N-methyl-N'-[2-(1-benzyl-4-(1,2,3-triazolyl)methylthio)-ethyl]thiourea.

Using 3-amino-5-hydroxymethyl-1,2,4-triazole and 3-mercaptopropylamine as starting materials in the procedure of Example 1 gives N-methyl-N'-[3-(3-amino-5-(1,2,4-triazolyl)-methylthio)propyl]thiourea.

EXAMPLE 175

Converting 5-methyl-4-(1,2,3-triazole)carboxylic acid to the methyl ester and reducing the ester with lithium aluminium hydride in tetrahydrofuran gives 4-hydroxymethyl-5-methyl-1,2,3-triazole.

Using 4-hydroxymethyl-5-methyl-1,2,3-triazole as the starting material in the procedure of Example 1 gives N-methyl-N'-[2-(5-methyl-4-(1,2,3-triazolyl)methylthio)-ethyl]thiourea.

By the same procedure, using 5-amino-4-(1,2,3-triazole)carboxylic acid, the product is N-methyl-N'-[2-(5-amino-4-(1,2,3-triazolyl)methylthio)ethyl]thiourea.

Similarly, using the following triazolecarboxylic acid compounds:
5-hydroxy-4-(1,2,3-triazole)carboxylic acid (prepared by alkaline hydrolysis of the corresponding ethyl ester)
4,5-(1,2,3-triazole)dicarboxylic acid
3-hydroxy-5-(1,2,4-triazole)carboxylic acid
the products are, respectively:
N-methyl-N'-[2-(5-hydroxy-4-(1,2,3-triazolyl)methylthio)ethyl]thiourea
4,5-bis-[2-(N-methylthioureido)ethylthiomethyl]-1,2,3-triazole
N-methyl-N'-[2-(3-hydroxy-5-(1,2,4-triazolyl)methylthio)-ethyl]thiourea.

Reduction of 3-chloro-5-(1,2,4-triazole)carboxylic acid with diborane gives the corresponding 5-hydroxymethyl compound and using this starting material in the procedure of Example 1 gives N-methyl-N'-[2-(3-chloro-5-(1,2,4-triazolyl)methylthio)ethyl]thiourea.

EXAMPLE 176

By the procedure of Example 21, using 3-mercapto-1,2,4-triazole as the starting material, the product is N-methyl-N'-[3-(3-(1,2,4-triazolyl)thio)propyl]thiourea.

By the same procedure, using 4-mercapto-1,2,3-triazole, the product is N-methyl-N'-[3-(4-(1,2,3-triazolyl)-thio)propyl]thiourea.

EXAMPLE 177

N-Methyl-N'-[2-(2-(3-(1,2,4-triazolyl))ethyl)thioethyl]thiourea

Using 3-(2-chloroethyl)-1,2,4-triazole as the starting material in the procedure of Example 17 gives the title compound.

EXAMPLE 178

Reaction of 3-(2-aminoethyl)thiomethyl-4-methyl-1,2,4-triazole with methyl isocyanate by the procedure of Example 24 gives N-methyl-N'-[2-(4-methyl-3-(1,2,4-triazolyl)-methylthio)ethyl]urea.

Similarly, reacting 4-(2-aminoethyl)thiomethyl-5-methyl-1,2,3-triazole (prepared from 4-hydroxymethyl-5-methyl-1,2,3-triazole by the procedure of Example 1) with methyl isocyanate gives N-methyl-N'-[2-(5-methyl-4-(1,2,3-triazolyl)-methylthio)ethyl]urea.

Using ethyl isocyante in place of methyl isocyanate in the above procedure gives the corresponding N-ethyl compounds.

EXAMPLE 179

N-Methyl-N'-[2-(3-(1,2,4-triazolyl)methoxy)ethyl]thiourea

By the procedure of Example 38, using 3-chloromethyl-1,2,4-triazole as the starting material, the product is the title compound.

EXAMPLE 180

Treatment of 3-(2-aminoethyl)thiomethyl-4-methyl-1,2,4-triazole with 2-dimethylaminoethyl isothiocyanate by the procedure of Example 1 gives N-(2-dimethylaminoethyl)-N'-[2-(4-methyl-3-(1,2,4-triazolyl)-methylthio)ethyl]thiourea.

By the same procedure, using 4-(2-aminoethyl)thiomethyl-5-methyl-1,2,3-triazole (prepared by reacting 4-hydroxymethyl-5-methyl-1,2,3-triazole with cysteamine hydrochloride) as the starting material, the product is N-(2-dimethylaminoethyl)-N'-[2-(5-methyl-4-(1,2,3-triazolyl)methylthio)ethyl]thiourea. Reacting with hydrobromic acid gives the hydrobromide salt.

EXAMPLE 181

By the procedure of Example 18, 3-(2-aminoethyl)-thiomethyl-4-methyl-1,2,4-triazole is reacted with benzoyl isothiocyanate to give N-benzoyl-N'-[2-(4-methyl-3-(1,2,4-triazolyl)methylthio)ethyl]thiourea. Removing the benzoyl group by the procedure of Example 18 gives N-[2-(4-methyl-3-(1,2,4-triazolyl)methylthio)ethyl]thiourea.

By the same procedure reacting 4-(2-aminoethyl)-thiomethyl-5-methyl-1,2,3-triazole with benzoyl isothiocyanate gives N-benzoyl-N'-[2-(5-methyl-4-(1,2,3-triazolyl)-methylthio)ethyl]thiourea and then removing the benzoyl group gives N-[2-(5-methyl-4-(1,2,3-triazolyl)methylthio)-ethyl]thiourea.

EXAMPLE 182

| Ingredients | Amounts |
|---|---|
| N-Methyl-N'-[2-(4-methyl-3-(1,2,4-triazolyl)-methylthio)ethyl]thiourea | 200 mg. |
| Lactose | 100 mg. |

The ingredients are mixed and filled into a hard gelatin capsule.

EXAMPLE 183

| Ingredients | Amounts |
|---|---|
| N-Methyl-N'-[2-(5-methyl-4-(1,2,3-triazolyl)-methylthio)ethyl]thiourea | 200 mg. |
| Sucrose | 70 mg. |
| Starch | 25 mg. |
| Talc | 5 mg. |
| Stearic acid | 2 mg. |

The ingredients are mixed and filled into a hard gelatin capsule.

Compounds of formula I wherein A is such that there is formed together with the carbon atom shown a triazole ring and Y is NH are exemplified by the following examples.

EXAMPLE 184

Using, in the procedure of Example 40, the following chloroalkyltriazoles (which may be prepared from the corresponding hydroxyalkyltriazoles by treating with thionyl chloride):
3-chloromethyl-1,2,4-triazole
3-(2-chloroethyl)-1,2,4-triazole
3-chloromethyl-4-methyl-1,2,4-triazole
3,5-di(chloromethyl)-1,2,4-triazole
3-chloromethyl-2-benzyl-1,2,4-triazole
3-amino-5-chloromethyl-1,2,4-triazole
3-bromo-5-chloromethyl-1,2,4-triazole
the following products are obtained, respectively:
N-methyl-N'-[2-(3-(1,2,4-triazolyl)methylamino)ethyl]-thiourea
N-methyl-N'-[2-(2-(3-(1,2,4-triazolyl))ethylamino)-ethyl]thiourea
N-methyl-N'-[2-(4-methyl-3-(1,2,4-triazolyl)methylamino)-ethyl]thiourea
3,5-bis-[2-(N-methylthioureido)ethylaminomethyl]-1,2,4triazole
N-methyl-N'-[2-(2-benzyl-3-(1,2,4-triazolyl)methylamino)-ethyl]thiourea
N-methyl-N'-[2-(3-amino-5-(1,2,4-triazolyl)methylamino)-ethyl]thiourea
N-methyl-N'-[2-(3-bromo-5-(1,2,4-triazolyl)methylamino)-ethyl]thiourea.

By the same procedure, using ethyl isothiocyanate in place of methyl isothiocyanate, the corresponding N-ethyl compounds are prepared.

Using, in the procedure of Example 40, 3-chloromethyl-1,2,4-triazole and 1,3-diaminopropane as the starting materials, the product is N-methyl-N'-[3-(3-(1,2,4-triazolyl)-methylamino)propyl]thiourea.

EXAMPLE 185

In the procedure of Example 40, using the following chloroalkyltriazoles, prepared from the corresponding hydroxyalkyl compounds by reacting with thionyl chloride:
1-benzyl-4-chloromethyl-1,2,3-triazole
4-chloromethyl-5-methyl-1,2,3-triazole
5-amino-4-chloromethyl-1,2,3-triazole
4-chloromethyl-5-hydroxy-1,2,3-triazole
4,5-di(chloromethyl)-1,2,3-triazole
3-chloro-5-chroromethyl-1,2,4-triazole
3-hydroxy-5-chloromethyl-1,2,4-triazole
the following products are obtained, respectively:
N-methyl-N'-[2-(1-benzyl-4-(1,2,3-triazolyl)methylamino)ethyl]thiourea
N-methyl-N'-[2-(5-methyl-4-(1,2,3-triazolyl)methylamino)-ethyl]thiourea
N-methyl-N'-[2-(5-amino-4-(1,2,3-triazolyl)methylamino)-ethyl]thiourea
N-methyl-N'-[2-(5-hydroxy-4-(1,2,3-triazolyl)methylamino)-ethyl]thiourea
4,5-bis-[2-(N-methylthioureido)ethylaminomethyl]-1,2,3-triazole
N-methyl-N'-[2-(3-chloro-5-(1,2,4-triazolyl)methylamino)-ethyl]thiourea
N-methyl-N'-[2-(3-hydroxy-5-(1,2,4-triazolyl)methylamino)-ethyl]thiourea.

EXAMPLE 186

Reacting N-(3-(1,2,4-triazolyl)methyl)ethylenediamine, prepared by reacting ethylenediamine with 3-chloromethyl-1,2,4-triazole, with methyl isocyanate by the procedure of Example 24, then concentrating and separating by column chromatography gives N-methyl-N'-[2-(3-(1,2,4-triazolyl)-methylamino)ethyl]urea. Treatment with hydriodic acid gives the hydroiodide salt.

EXAMPLE 187

Treating N-(3-(1,2,4-triazolyl)methyl)ethylenediamine with 2-dimethylaminoethyl isothiocyanate by the procedure of Example 40, then concentrating and separating by column chromatography gives N-(2-dimethylaminoethyl)-N'-[2-(3-(1,2,4-triazolyl)methylamino)ethyl]thiourea.

By the same procedure, using N-(5-methyl-4-(1,2,3-triazolyl)methyl)ethylenediamine, prepared by reacting ethylenediamine with 4-chloromethyl-5-methyl-1,2,3-triazole, the product is N-(2-diamethylaminoethy)-N'-[2-(5-methyl-4-(1,2,3-triazolyl)methylamino)ethyl]thiourea.

EXAMPLE 188

A mixture of 3-chloro-1,2,4-triazole (10.3 g., 0.1 m.) and 1,3-diaminopropane (7.4 g., 0.1 m.) in ethanol containing sodium ethoxide is allowed to stand overnight. The solvent is removed to give 3-(3-aminopropylamino)-1,2,4-triazole. This intermediate is reacted with methyl isothiocyanate to give N-methyl-N'-[3-(3-(1,2,4-triazolyl)amino)propyl]thiourea.

By the same procedure, using 4-chloro-5-methyl-1,2,3-triazole as the starting material, the intermediate 4-(3-aminopropylamino)-5-methyl-1,2,3-triazole and the product N-methyl-N'-[3-(5-methyl-4-(1,2,3-triazolyl)amino)-propyl]thiourea are prepared.

EXAMPLE 189

By the procedure of Example 46, reacting 3-(3-aminopropylamino)-1,2,4-triazole with benzoyl isothiocyanate gives N-benzoyl-N'-[3-(3-(1,2,4-triazolyl)amino)propyl]thiourea. Removing the benzoyl group by the procedure of Example 46 gives N-[3-(3-(1,2,4-triazolyl)amino)propyl]thiourea.

By the same procedure, reacting 4-(3-aminopropylamino)-5-methyl-1,2,3-triazole with benzoyl isothiocyanate gives N-benzoyl-N'-[3-(5-methyl-4-(1,2,3-triazolyl)amino)-propyl]thiourea and removing the benzoyl group gives N-[3-(5-methyl-4-(1,2,3-triazolyl)amino)propyl]thiourea.

EXAMPLE 190

| Ingredients | Amounts |
| --- | --- |
| N-Methyl-N'-[2-(3-(1,2,4-triazolyl)methylamino)ethyl]thiourea | 200 mg. |
| Lactose | 100 mg. |

The ingredients are mixed and filled into a hard gelatin capsule.

Similarly, a capsule is prepared using 200 mg. of N-methyl-N'-[2-(5-methyl-4-(1,2,3-triazolyl)methylamino)-ethyl]thiourea.

Compounds of formula I wherein A is such that there is formed together with the carbon atom shown a thiadiazole ring and Y is oxygen or sulphur (sulphur is preferred) are exemplified by the following examples.

EXAMPLE 191

N-Methyl-N'-[2-(2-amino-5-(1,3,4-thiadiazolyl)methylthio)-ethyl]thiourea

By the procedure of Example 1, the following intermediate amine salt was prepared: 2-amino-5-(2-aminoethyl)thiomethyl-1,3,4-thiadiazole dihydrobromide, m.p. 229°–232° C.

Reacting this intermediate amine salt with methyl isothiocyanate by the procedure of Example 1(ii) gave N-methyl-N'-[2-(2-amino-5-(1,3,4-thiadiazolyl)methylthio)-ethyl]thiourea, recrystallised from aqueous ethanol, m.p. 143°–145° C. (Found: C, 32.0; H, 5.0; N, 26.7; S, 36.2. $C_7H_{13}N_5S_3$ requires: C, 32.0; H, 5.0; N, 26.6; S, 36.5).

EXAMPLE 192

N-Methyl-N'-[3-(2-amino-5-(1,3,4-thiadiazolyl)thio)-propyl]thiourea

By the procedure of Example 21(i), using 2-amino-5-mercapto-1,3,4-thiadiazole as the starting material, the following intermediate dihydrobromide salt was prepared: 2-amino-5-(3-aminopropylthio)-1,3,4-thiadiazole dihydrobromide, m.p. 185°–188° C.

Reacting this intermediate with methyl isothiocyanate by the procedure of Example 21(ii) gave N-methyl-N'-[3-(2-amino-5-(1,3,4-thiadiazolyl)thio)propyl]thiourea, recrystallised from ethanol-ether, m.p. 109°–110° C. (Found: C, 31.5; H, 5.0; N, 26.2; S, 36.1. $C_7H_{13}N_5S_3$ requires: C, 31.9; H, 5.0; N, 26.6; S, 36.5).

EXAMPLE 193

Using 5-chloro-3-chloromethyl-1,2,4-thiadiazole as the starting material in the procedure of Example 1, the product is N-methyl-N'-[2-(5-chloro-3-(1,2,4-thiadiazolyl)-methylthio)ethyl]thiourea.

By the same procedure using ethyl isothiocyanate in place of methyl isothiocyanate, the corresponding N-ethyl compound is prepared.

Using 5-chloro-3-chloromethyl-1,2,4-thiadiazole and 3-mercaptopropylamine as starting materials in the procedure of Example 1 gives N-methyl-N'-[3-(5-chloro-3-(1,2,4-thiadiazolyl)methylthio)propyl]thiourea.

EXAMPLE 194

N-Methyl-N'-[3-(2-trifluoromethyl-5-(1,3,4-thiadiazolyl)thio)-propyl]thiourea

By the procedure of Example 21, using 2-trifluoromethyl-5-mercapto-1,3,4-thiadiazole as the starting material, the product is the title compound.

EXAMPLE 195

Using 2-mercapto-1,3,4-thiadiazole as the starting material in the procedure of Example 21 gives N-methyl-N'-[3-(2-(1,3,4-thiadiazolyl)thio)propyl]thiourea.

Similarly, using 3-mercapto-1,2,4-thiadiazole as the starting material, the product is N-methyl-N'-[3-(3-(1,2,4-thiadiazolyl)thio)propyl]thiourea.

EXAMPLE 196

N-Methyl-N'-[2-(4-(1,2,3,-thiadiazolyl)methylthio)ethyl]thiourea

Using 4-hydroxymethyl-1,2,3-thiadiazole as the starting material in the procedure of Example 1 gives the title compound.

EXAMPLE 197

Converting 5-methyl-4-(1,2,3-thiadiazole)carboxylic acid to the methyl ester and reducing the ester with lithium aluminium hydride in tetrahydrofuran gives 4-hydroxymethyl-5-methyl-1,2,3-thiadiazole.

Using 4-hydroxymethyl-5-methyl-1,2,3-thiadiazole as the starting material in the procedure of Example 1 gives N-methyl-N'-[2-(5-methyl-4-(1,2,3-thiadiazolyl)-methylthio)-ethyl]thiourea.

By the same procedure using the following as starting materials (prepared from the corresponding carboxylic acids by the above process or in the case of the 4-chloro substituted compound by treatment with diborane):

5-amino-4-hydroxymethyl-1,2,3-thiadiazole
4,5-di(hydroxymethyl)-1,2,3-thiadiazole
4-hydroxy-3-hydroxymethyl-1,2,5-thiadiazole
4-chloro-3-hydroxymethyl-1,2,5-thiadiazole the following products are obtained, respectively:

N-methyl-N'-[2-(5-amino-4-(1,2,3-thiadiazolyl)methylthio)-ethyl]thiourea
4,5-bis-[2-(N-methylthioureido)ethylthiomethyl]-1,2,3-thiadiazole
N-methyl-N'-[2-(4-hydroxy-3-(1,2,5-thiadiazolyl)-methylthio)ethyl]thiourea
N-methyl-N'-[2-(4-chloro-3-(1,2,5-thiadiazolyl)-methyl-thio)ethyl]thiourea.

EXAMPLE 198

N-Methyl-N'-[2-(2-(2-amino-5-(1,3,4-thiadiazolyl)ethyl)-thioethyl]thiourea

2-Amino-5-(1,3,4-thiadiazole)acetic acid is esterified with anhydrous ethanolic hydrogen chloride and the resulting ethyl ester is reduced with lithium aluminium hydride in tetrahydrofuran to give 2-amino-5-(2-hydroxyethyl)-1,3,4-thiadiazole. Treating this hydroxyethyl compound with thionyl chloride gives 2-amino-5-(2-chloroethyl)-1,3,4-thiadiazole.

Using 2-amino-5-(2-chloroethyl)-1,3,4-thiadiazole as the starting material in the procedure of Example 17 gives the title compound.

EXAMPLE 199

N-Methyl-N'-[3-(2-amino-5-(1,3,4-thiadiazolyl)thio)-propyl]urea

By the procedure of Example 24, 2-amino-5-(3-aminopropylthio)-1,3,4-thiadiazole is reacted with methyl isocyanate to give the title compound.

EXAMPLE 200

N-Methyl-N'-[2-(5-methyl-4-(1,2,3-thiadiazolyl)methoxy)ethyl]-thiourea

By the procedure of Example 38, using 4-chloromethyl-5-methyl-1,2,3-thiadiazole (prepared by reacting 4-hydroxymethyl-5-methyl-1,2,3-thiadiazole with thionyl chloride) as the atarting material, the title compound is prepared.

EXAMPLE 201

By the procedure of Example 18, 2-amino-5-(3-aminopropylthio)-1,3,4-thiadiazole is reacted with benzoyl isothiocyanate to give N-benzoyl-N'-[3-(2-amino-5-(1,3,4-thiadiazolyl)thio)propyl]thiourea. Removing the benzoyl group by the procedure of Example 18 gives N-[3-(2-amino-5-(1,3,4-thiadiazolyl)thio)-propyl]thiourea. Treatment with hydrochloric acid gives the hydrochloride salt.

EXAMPLE 202

N-(2-Dimethylaminoethyl)-N'-[3-(2-amino-5-(1,3,4-thiadiazolyl)-thiopropyl]thiourea Treatment of 2-amino-5-(3-aminopropylthio)-1,3,4-thiadiazole with 2-dimethylaminoethyl isothiocyanate by the procedure of Example 1 gives the title compound.

EXAMPLE 203

| Ingredients | Amounts |
| --- | --- |
| N-Methyl-N'-[3-(2-amino-5-(1,3,4-thiadiazolyl)-thio)propyl]thiourea | 200 mg. |
| Sucrose | 70 mg. |
| Starch | 25 mg. |
| Talc | 5 mg. |
| Stearic acid | 2 mg. |

The ingredients are mixed and filled into a hard gelatin capsule.

Compounds of formula I wherein A is such that there is formed together with the carbon atom shown a thiadiazole ring and Y is NH are exemplified by the following examples.

EXAMPLE 204

Using, in the procedure of Example 40, the following chloroalkylthiadiazoles (which may be prepared by treating the corresponding hydroxyalkyl compounds with thionyl chloride):

2-amino-5-chloromethyl-1,3,4-thiadiazole
5-chloro-3-chloromethyl-1,2,4-thiadiazole
4-chloromethyl-1,2,3-thiadiazole
3-chloromethyl-4-hydroxy-1,2,5-thiadiazole
4-chloromethyl-5-methyl-1,2,3-thiadiazole
2-amino-5-(2-chloroethyl)-1,3,4-thiadiazole
4,5-di(chloromethyl)-1,2,3-thiadiazole the following products are obtained, respectively:

N-methyl-N'-[2-(2-amino-5-(1,3,4-thiadiazolyl)methylamino)ethyl]thiourea
N-methyl-N'-[2-(5-chloro-3-(1,2,4-thiadiazolyl)methylamino)ethyl]thiourea
N-methyl-N'-[2-(4-(1,2,3-thiadiazolyl)methylamino)- ethyl]thiourea
N-methyl-N'-[2-(4-hydroxy-3-(1,2,5-thiadiazolyl)-methyl-amino)ethyl]thiourea
N-methyl-N'-[2-(5-methyl-4-(1,2,3-thiadiazolyl)methylamino)ethyl]thiourea
N-methyl-N'-[2-(2-(2-amino-5-(1,3,4-thiadiazolyl))ethylamino)ethyl]thiourea
4,5-bis-[2-(N-methylthioureido)ethylaminomethyl]-1,2,3-thiadiazole.

Using, in the procedure of Example 40, 2-amino-5-chloromethyl-1,3,4-thiadiazole and 1,3-diaminopropane as the starting materials, the product is N-methyl-N'-[3-(2-amino-5-(1,3,4-thiadiazolyl)methylamino)-propyl]thiourea.

EXAMPLE 205

Reacting N-(5-amino-2-(1,3,4-thiadiazolyl)methyl)-ethylenediamine, prepared by reacting ethylenediamine with 5-amino-2-chloromethyl-1,3,4-thiadiazole, with methyl isocyanate by the procedure of Example 24, then concentrating and separating the residue by column chromatography gives N-methyl-N'-[2-(5-amino-2-(1,3,4-thiadiazolyl)methylamino)-ethyl]urea.

By the same procedure, using ethyl isocyanate the corresponding N-ethyl compound is prepared.

EXAMPLE 206

Treating N-(5-amino-2-(1,3,4-thiadiazolyl)methy)-ethylenediamine with 2-dimethylaminoethyl isothiocyanate by the procedure of Example 40, then concentrating and separating by column chromatography gives N-(2-dimethylamino-ethyl)-N'-[2-(5-amino-2-(1,3,4-thiadiazolyl)methylamino)ethyl]-thiourea. Treating with maleic acid in ethanol gives the maleate salt.

EXAMPLE 207

By the procedure of Example 188, 2-bromo-1,3,4-thiadiazole is reacted with 1,3-diaminopropane to give 2-(3-aminopropylamino)-1,3,4-thiadiazole and this intermediate is reacted with methyl isothiocyanate to give N-methyl-N'-[3-(2-(1,3,4-thiadiazolyl)amino)-propyl]thiourea.

Similarly, using 3-chloro-1,2,5-thiadiazole as the starting material, the intermediate 3-(3-aminopropylamino)-1,2,5-thiadiazole and the product N-methyl-N'-[3-(3-(1,2,5-thiadiazolyl)amino)propyl]thiourea are prepared.

Also, using 2-bromo-5-trifluoromethyl-1,3,4-thiadiazole as the starting material, the intermediate 2-(3-aminopropylamino)-5-trifluoromethyl-1,3,4-thiadiazole and the product N-methyl-N'-[3-(5-trifluoromethyl-2-(1,3,4-thiadiazolyl)amino)propyl]thiourea are prepared.

Reaction of 3-amino-1,2,4-thiadiazole with 3-phthalimidopropyl bromide and hydrazinolysis of the product gives 3-(3-aminopropylamino)-1,2,4-thiadiazole and from this intermediate N-methyl-N'-[3-(3-(1,2,4-thiadiazolyl)-amino)propyl]thiourea is prepared.

EXAMPLE 208

By the procedure of Example 46, reacting 2-(3-aminopropylamino)-1,3,4-thiadiazole with benzoyl isothiocyanate gives N-benzoyl-N'-[3-(2-(1,3,4-thiadiazolyl)amino)propyl]-thiourea. Removing the benzoyl group by the procedure of Example 46 gives N-[3-(2-(1,3,4-thiadiazolyl)amino)propyl]-thiourea.

EXAMPLE 209

| Ingredients | Amounts |
| --- | --- |
| N-Methyl-N'-[3-(2-(1,3,4-thiadiazolyl)amino)-propyl]thiourea | 200 mg. |
| Lactose | 100 mg. |

The ingredients are mixed and filled into a hard gelatin capsule.

Compounds of formula I wherein A is such that there is formed together with the carbon atom shown a benzimidazole ring and Y is oxygen or sulphur (sulphur is preferred) are exemplified by the following examples.

EXAMPLE 210

By the process of Example 1 the following intermediate amine salt was prepared: 2-[(2-aminoethyl)-thiomethyl]benzimidazole dihydrobromide, m.p. 242°–245° C.

Reaction of this intermediate amine salt with methyl isothiocyanate by the procedure of Example 1(ii) gave N-methyl-N'-[2-(2-benzimidazolylmethylthio)ethyl]-thiourea, recrystallised from isopropanol/isopropyl acetate, m.p. 157°–159° C. (Found: C, 51.3; H, 5.8; N, 19.9; S, 22.5. $C_{12}H_{16}N_4S_2$ requires: C, 51.4; H, 5.8; N, 20.0; S, 22.9).

EXAMPLE 211

N-Methyl-N'-[2-(2-(2-benzimidazolyl)ethyl)thioethyl]thiourea

Using 2-(2-chloroethyl)benzimidazole, prepared by treating 2-(2-hydroxyethyl)benzimidazole with thionyl chloride, as the starting material in the procedure of Example 17 gives the title compound.

EXAMPLE 212

N-Methyl-N'-[2-(2-benzimidazolylmethylthio)ethyl]urea

By the procedure of Example 24, 2-[(2-aminoethyl)-thiomethyl]benzimidazole is reacted with methyl isocyanate to give the title compound.

EXAMPLE 213

Using 2-chloromethylbenzimidazole (prepared by reacting 2-hydroxymethylbenzimidazole with thionyl chloride) as the starting material in the procedure of Example 38 gives N-methyl-N'-[2-(2-benzimidazolylmethoxy)ethyl]thiourea.

Using 2-chloromethylbenzimidazole as the starting material in the procedure of Example 28 gives N-methyl-N'-[3-(2-benzimidazolylmethoxy)propyl]thiourea.

EXAMPLE 214

By the procedure of Example 21, using 2-mercaptobenzimidazole as the starting material, N-methyl-N'-[3-(2-benzimidazolylthio)propyl]thiourea is obtained. Reacting with hydrobromic acid gives the hydrobromide salt.

Using ethyl isothiocyanate in place of methyl isothiocyanate in the above procedure gives the corresponding N-ethyl compound.

EXAMPLE 215

Benzoyl isothiocyanate is reacted with 2-[(2-aminoethyl)thiomethyl]benzimidazole by the procedure of Example 18 to give N-benzoyl-N'-[2-(2-benzimidazolylmethylthio)ethyl]thiourea. Removing the benzoyl group by the procedure of Example 18 gives N-[2-(2-benzimidazolylmethylthio)ethyl]thiourea.

EXAMPLE 216

N-(2-Dimethylaminoethyl)-N'-[2-(2-benzimidazolylmethylthio)ethyl]thiourea

Treatment of 2-[(2-aminoethyl)thiomethyl]benzimidazole with 2-dimethylaminoethyl isothiocyanate by the procedure of Example 1 gives the title compound.

EXAMPLE 217

| Ingredients | Amounts |
|---|---|
| N-Methyl-N'-[2-(2-benzimidazolylmethylthio)-ethyl]thiourea | 200 mg. |
| Lactose | 100 mg. |

The ingredients are mixed and filled into a hard gelatin capsule.

Compounds of formula I wherein A is such that there is formed together with the carbon atom shown a benzimidazole ring and Y is NH are exemplified by the following examples.

EXAMPLE 218

Using 2-chloromethylbenzimidazole in the procedure of Example 40 gives N-methyl-N'-[2-(2-benzimidazolylmethyl-amino)ethyl]thiourea.

Similarly, using 2-(2chloroethyl)benzimidazole, the product is N-methyl-N'-[2-(2-(2-benzimidazolyl)ethylamino)-ethyl]thiourea. Reacting with hydrochloric acid gives the hydrochloride salt.

EXAMPLE 219

N-Methyl-N'-[2-(2-benzimidazolylmethylamino)ethyl]urea

Reacting N-(2-benzimidazolylmethyl)ethylenediamine, prepared by reacting ethylenediamine with 2-chloromethylbenzimidazole by the procedure of Example 40, with methyl isocyanate by the procedure of Example 24 and then concentrating and separating the residue by column chromatography gives the title compound.

Using 2-chloromethylbenzimidazole and 1,3-diaminopropane as the starting materials in the procedure of Example 40 gives N-methyl-N'-[3-(2-benzimidazolylmethylamino)propyl]thiourea.

EXAMPLE 220

N-Methyl-N'-[3-(2-benzimidazolylamino)propyl]thiourea

Using 2-aminobenzimidazole as the starting material in the procedure of Example 53 gives 2-(3-aminopropylamino)-benzimidazole as the intermediate and reacting that intermediate with methyl isothiocyanate gives the title compound.

EXAMPLE 221

N-(2-Dimethylaminoethyl)-N'-[2-(2-benzimidazolylmethylamino)ethyl]thiourea

N-(2-Benzimidazolylmethyl)ethylenediamine, prepared by reacting ethylenediamine with 2-chloromethylbenzimidazole by the procedure of Example 40, is reacted with 2-dimethylaminoethyl isothiocyanate by the procedure of Example 40 to give the title compound.

EXAMPLE 222

Reacting 2-(3-aminopropylamino)benzimidazole with benzoyl isothiocyanate by the procedure of Example 46 gives N-benzoyl-N'-[3-(2-benzimidazolylamino)propyl]thiourea.

Removing the benzoyl group by the procedure of Example 46 gives N-[3-(2-benzimidazolylamino)propyl]thiourea. Reacting with hydrobromic acid gives the dihydrobromide salt.

EXAMPLE 223

| Ingredients | Amounts |
|---|---|
| N-Methyl-N'-[2-(2-benzimidazolylmethylamino)-ethyl]thiourea | 200 mg. |
| Lactose | 100 mg. |

The ingredients are mixed and filled into a hard gelatin capsule.

Compounds of formula I wherein A is such that there is formed together with the carbon atom shown a 5,6,7,8-tetrahydroimidazo[1,5-a]pyridine ring and Y is oxygen or sulphur (sulphur is preferred) are exemplified by the following examples.

EXAMPLE 224

N-Methyl-N'-[2-(3-(5,6,7,8-tetrahydroimidazo[1,5-a]pyridyl)-methylthio)ethyl]thiourea A solution of 1.58 molar n-butyl lithium in n-hexane (49 ml.) was added over 0.5 hour to a stirred solution of 5,6,7,8-tetrahydroimidazo[1,5-a]pyridine (8.9 g.) in dry ether at −60° under nitrogen. After 3 hours, gaseous formaldehyde generated by the thermal condensation of paraformaldehyde (6.9 g.) was passed into the red solution. The mixture was allowed to warm to room temperature overnight, acidified with hydrochloric acid and extracted with chloroform. The aqueous layer was basified with an excess of saturated sodium carbonate solution and extracted with chloroform. Concentration and recrystallisation of the residue from ethanol-ethyl acetate-petroleum ether afforded 3-hydroxymethyl-5,6,7,8-tetrahydroimidazo[1,5-a]pyridine (7.7 g.), m.p. 188°–199°.

Reacting 3-hydroxymethyl-5,6,7,8-tetrahydroimidazo-[1,5-a]pryidine with cysteamine hydrochloride by the procedure of Example 1(i)(a) gave the following intermediate amine salt: 3-[(2-aminoethyl)-thiomethyl]-5,6,7,8-tetrahydroimidazo[1,5-a]pyridine dihydrobromide.

Reacting the above prepared intermediate amine salt with methyl isothiocyanate by the procedure of Example 1(ii) gave N-methyl-N'-[2-(3-(5,6,7,8-tetrahydroimidazo[1,5-a]pyridyl)methylthio)ethyl]thiourea, recrystallised from isopropyl acetate/ethyl acetate, m.p. 105°–106° C. (Found:
, 50.7; H, 7.1; N, 19.6; S, 22.3. $C_{12}H_{20}N_4S_2$ requires: C, 50.7; H, 7.1; N, 19.7; S, 22.5).

EXAMPLE 225

By the procedure of Example 28, using 3-chloromethyl-5,6,7,8-tetrahydroimidazo[1,5-a]pyridine, prepared by reacting the 3-hydroxymethyl compound with thionyl chloride, as the starting material, N-methyl-N'-[3-(3-(5,6,7,8-tetrahydroimidazo[1,5-a]pyridyl)methoxy)propyl]thiourea is prepared. Reacting with hydriodic acid gives the hydroiodide salt.

EXAMPLE 226

By the procedure of Example 24, 3-[(2-aminoethyl)-thiomethyl]-5,6,7,8-tetrahydroimidazo[1,5-a]pyridine is reacted with methyl isocyanate to give N-methyl-N'-

[2-(3-(5,6,7,8-tetrahydroimidazo[1,5-a]pyridyl)me-thylthio)ethyl]urea.

By the same procedure, using ethyl isocyanate the corresponding N-ethyl compound is obtained.

EXAMPLE 227

By the procedure of Example 18, 3-[(2-aminoethyl)-thiomethyl]-5,6,7,8-tetrahydroimidazo[1,5-a]pyridine is reacted with benzoyl isothiocyanate to give N-benzoyl-N'-[2-(3-(5,6,7,8-tetrahydroimidazo[1,5-a]pyridyl)methylthio)-ethyl]thiourea. Removing the benzoyl group by the procedure of Example 18 gives N-[2-(3-(5,6,7,8-tetrahydroimidazo(1,5-a]-pyridyl)-methylthio)ethyl]thiourea.

EXAMPLE 228

N-(2-Dimethylaminoethyl)-N'-[2-(3-(5,6,7,8-tetrahydroimidazo[1,5-a]pyridyl)methylthio)ethyl]thiourea Treatment of 3-[(2-aminoethyl)thiomethyl]-5,6,7,8-tetrahydroimidazo[1,5-a]pyridine with 2-dimethylaminoethyl isothiocyanate gives the title compound.

EXAMPLE 229

| Ingredients | Amounts |
| --- | --- |
| N-Methyl-N'-[2-(3-(5,6,7,8-tetrahydroimidazo-[1,5-a]pyridyl)methylthio)ethyl]thiourea | 200 mg. |
| Lactose | 100 mg. |

The ingredients are mixed and filled into a hard gelatin capsule.

Compounds of formula I wherein A is such that there is formed together with the carbon atom shown a 5,6,7,8-tetrahydroimidazo[1,5-a]pyridine ring and Y is NH are exemplified by the following examples.

EXAMPLE 230

Using 3-chloromethyl-5,6,7,8-tetrahydroimidazo[1,5-a]pyridine, prepared by treating the corresponding 3-hydroxymethyl compound with thionyl chloride, as the starting material in the procedure of Example 40 gives N-methyl-N'-[2-(3-(5,6,7,8-tetrahydroimidazo[1,5-a]pyridyl)-methylamino)ethyl]thiourea. Treating with hydrobromic acid gives the hydrobromide salt.

By the same procedure, using ethyl isothiocyanate in place of methyl isothiocyanate, gives the corresponding N-ethyl compound.

EXAMPLE 231

N-Methyl-N'-[2-(3-(5,6,7,8-tetrahydroimidazo[1,5-a]pyridyl)-methylamino)ethyl]urea N-(3-(5,6,7,8-Tetrahydroimidazo[1,5-a]pyridyl)-methyl)ethylenediamine, prepared by reacting ethylenediamine with 3-chloromethyl-5,6,7,8-tetrahydroimidazo[1,5-a]pyridine by the procedure of Example 40, is reacted with methyl isocyanate by the procedure of Example 24 to give, after concentrating and separating by column chromatography, the title compound.

EXAMPLE 232

N-(2-Dimethylaminoethyl)-N'-[2-(3-(5,6,7,8-tetrahydroimidazo[1,5-a]pyridyl)methylamino)ethyl]thiourea Reacting N-(3-(5,6,7,8-tetrahydroimidazo[1,5-a]pyridyl)methyl)ethylenediamine with 2-dimethylaminoethyl isothiocyanate by the procedure of Example 40(a)(ii) gives the title compound.

EXAMPLE 233

By the procedure of Example 46, N-(3-(5,6,7,8-tetrahydroimidazo[1,5-a]pyridyl)methyl)ethylenediamine is reacted with benzoyl isothiocyanate and the benzoyl group is removed to give N-[2-(3-(5,6,7,8-tetrahydroimidazo[1,5-a]-pyridyl)methylamino)ethyl]-thiourea.

EXAMPLE 234

N-Methyl-N'-[3-(3-(5,6,7,8-tetrahydroimidazo[1,5-a]pyridyl)-methylamino)propyl]thiourea Using as the starting materials in the procedure of Example 40, 1,3-diaminopropane and 3-chloromethyl-5,6,7,8-tetrahydroimidazo[1,5-a]pyridine, the title compound is prepared.

EXAMPLE 235

| Ingredients | Amounts |
| --- | --- |
| N-Methyl-N'-[2-(3-(5,6,7,8-tetrahydroimidazo-[1,5-a]pyridyl)methylamino)ethyl]thiourea | 200 mg. |
| Lactose | 100 mg. |

The ingredients are mixed and filled into a hard gelatin capsule.

The pharmaceutical compositions prepared as in the foregoing examples are administered to a subject within the dose ranges given hereabove to inhibit H-2 histamine receptors.

In the forgoing examples, the temperatures are in degrees Centigrade.

What we claim is:

1. A pharmaceutical composition to inhibit H-2 histamine receptors comprising a pharmaceutical carrier and in an effective amount to inhibit said receptors a heterocyclic compound of the formula:

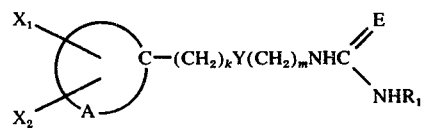

wherein A is such that there is formed together with the carbon atom shown an unsaturated heterocyclic nucleus, said unsaturated heterocyclic nucleus being an imidazole or pyrazole ring; $X_1$ is hydrogen, lower alkyl, hydroxyl, trifluoromethyl, benzyl, halogen, amino or

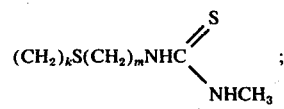

$X_2$ is hydrogen or when $X_1$ is lower alkyl, lower alkyl or halogen; $k$ is 0 to 2 and $m$ is 2 or 3, provided that the sum of $k$ and $m$ is 3 or 4; Y is oxygen, sulphur or NH; E is oxygen or sulphur; and $R_1$ is hydrogen, lower alkyl, benzoyl or di-lower alkylamino-lower alkyl or a pharmaceutically acceptable addition salt thereof with the proviso that $X_1$ is

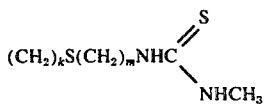

only when Y and E are sulphur and $R_1$ is methyl and with the proviso that when $X_1$ is other than hydrogen or lower alkyl and $X_2$ is other than hydrogen, $X_1$ and $X_2$ are attached at carbon atoms.

2. A pharmaceutical composition of claim 1 in which the heterocyclic compound is N-methyl-N'-[2-((5-methyl-4-imidazolyl)methylthio)ethyl]thiourea.

3. A pharmaceutical composition of calim 1 in which the pharmaceutical composition is in the form of a tablet or capsule.

4. A pharmaceutical composition of claim 1 in which the heterocyclic compound is present in an amount of from about 50 mg. to about 250 mg.

5. A method of inhibiting H-2 histamine receptors which comprises administering to an animal in need of inhibition of said receptors in an effective amount to inhibit said receptors a heterocyclic compound of the formula:

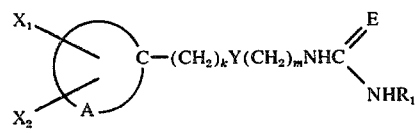

wherein A is such that there is formed together with the carbon atom shown an unsaturated heterocyclic nucleus, said unsaturated heterocyclic nucleus being an imidazole or pyrazole ring; $X_1$ is hydrogen, lower alkyl, hydroxyl, trifluoromethyl, benzyl, halogen, amino or

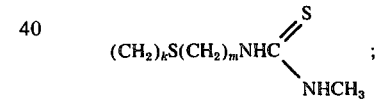

$X_2$ is hydrogen or when $X_1$ is lower alkyl, lower alkyl or halogen; $k$ is 0 to 2 and $m$ is 2 or 3, provided that the sum of $k$ and $m$ is 3 or 4; Y is oxygen, sulphur or NH; E is oxygen or sulphur; and $R_1$ is hydrogen, lower alkyl, benzoyl or di-lower alkylamino-lower alkyl or a pharmaceutically acceptable addition salt thereof with the proviso that $X_1$ is

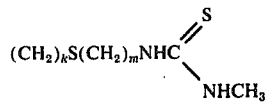

only when Y and E are sulphur and $R_1$ is methyl and with the proviso that when $X_1$ is other than hydrogen or lower alkyl and $X_2$ is other than hydrogen, $X_1$ and $X_2$ are attached at carbon atoms.

6. A method of claim 5 in which the heterocyclic compound is N-methyl-N'-[2-((5-methyl-4-imidazolyl)methylthio)ethyl]thiourea.

7. A method of claim 5 in which the heterocyclic compound is administered orally.

8. A method of claim 5 in which the heterocyclic compound is administered in a daily dosage regimen of from about 150 mg. to about 1000 mg.

9. A method of inhibiting gastric acid secretion which comprises administering to an animal in need of inhibition of gastric acid secretion in an effective amount to inhibit gastric acid secretion a heterocyclic compound of the formula:

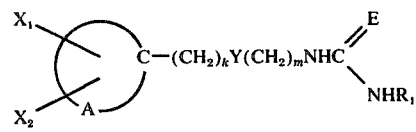

wherein A is such that there is formed together with the carbon atom shown an unsaturated heterocyclic nucleus, said unsaturated heterocyclic nucleus being an imidazole or pyrazole ring; $X_1$ is hydrogen, lower alkyl, hydroxyl, trifluoromethyl, benzyl, halogen, amino or

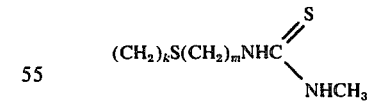

$X_2$ is hydrogen or when $X_1$ is lower alkyl, lower alkyl or halogen; $k$ is 0 to 2 and $m$ is 2 or 3, provided that the sum of $k$ and $m$ is 3 or 4; Y is oxygen, sulphur or NH; E is oxygen or sulphur; and $R_1$ is hydrogen, lower alkyl, benzoyl or di-lower alkylamino-lower alkyl or a pharmaceutically acceptable addition salt thereof with the proviso that $X_1$ is only when Y and E are sulphur and $R_1$ is methyl and with the proviso that when $X_1$ is other than hydrogen or lower alkyl and $X_2$ is other than hydrogen, $X_1$ and $X_2$ are attached at carbon atoms.

10. A method of claim 9 in which the heterocyclic compound is N-methyl-N'-[2-((5-methyl-4-imidazolyl)methylthio)-ethyl]thiourea.

* * * * *

UNITED STATES PATENT AND TRADEMARK OFFICE
CERTIFICATE OF CORRECTION

PATENT NO. : 4,018,931
DATED : April 19, 1977
INVENTOR(S) : Graham John Durant, John Colin Emmett and Charon Robin Ganellin It is certified that error appears in the above—identified patent and that said Letters Patent are hereby corrected as shown below:

On the first page of the patent, in the left-hand column, following item [60] insert the following:

[30]    Foreign Application Priority Data

March 9, 1971    United Kingdom 6352/71
    July 22, 1971    United Kingdom 34334/71
    August 8, 1972    United Kingdom 37015/72
    February 3, 1972    Ireland 136/72

Column 65, line 24, "calim" should read -- claim -- .

Signed and Sealed this sixteenth Day of August 1977

[SEAL]

Attest:

RUTH C. MASON
*Attesting Officer*

C. MARSHALL DANN
*Commissioner of Patents and Trademarks*